(12) United States Patent
Nitka et al.

(10) Patent No.: US 8,882,655 B2
(45) Date of Patent: Nov. 11, 2014

(54) IMPLANTABLE ACCESS PORT SYSTEM

(71) Applicant: Apollo Endosurgery, Inc., Austin, TX (US)

(72) Inventors: Greg Nitka, Santa Barbara, CA (US); Edwin J. Kayda, Santa Barbara, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 0 days.

(21) Appl. No.: 13/895,118

(22) Filed: May 15, 2013

(65) Prior Publication Data

US 2013/0253263 A1 Sep. 26, 2013

Related U.S. Application Data

(63) Continuation of application No. 12/881,460, filed on Sep. 14, 2010, now abandoned.

(51) Int. Cl.
*A61F 5/00* (2006.01)
*A61M 39/02* (2006.01)

(52) U.S. Cl.
CPC .......... *A61F 5/0066* (2013.01); *A61M 39/0208* (2013.01); *A61M 2039/0261* (2013.01); *A61M 39/0247* (2013.01); *A61M 2039/0223* (2013.01)
USPC .......................................................... 600/37

(58) Field of Classification Search
CPC ............. A61M 2039/0261; A61M 2039/0223; A61M 2025/0246; A61M 25/02
USPC .................. 600/37, 29–31; 128/879–899; 604/891.1, 288.03, 288.04, 288.02, 604/513, 502, 93.01, 175, 288; 606/219, 606/213, 217, 139
See application file for complete search history.

(56) References Cited

U.S. PATENT DOCUMENTS

| 586,113 | A | 7/1897 | Bott |
| 2,163,048 | A | 6/1939 | Mckee |

(Continued)

FOREIGN PATENT DOCUMENTS

| CN | 1250382 A | 4/2000 |
| CN | 1367670 A | 9/2002 |

(Continued)

OTHER PUBLICATIONS

Autumn K. et al.; 'Evidence of Van Der Waals Adhesion in Gecko Setae'; PNAS; vol. 99; No. 19; pp. 12252-12256; Sep. 17, 2012.

(Continued)

*Primary Examiner* — Christine Matthews
*Assistant Examiner* — Joshua D Lannu
(74) *Attorney, Agent, or Firm* — Gordon & Jacobson, PC

(57) ABSTRACT

An implantable injection port comprises a base. A first gear is coupled to the base, and a first anchor is coupled to the first gear. A second gear is coupled to the base, and a second anchor is coupled to the second gear. A top portion of the injection port is spaced apart from the base of the port and has a first plurality of top teeth that engage with a first plurality of gear teeth on the first gear. This engagement occurs prior to rotation of the second gear. The top portion rotates, which causes rotation of the first gear, which in turn causes movement of the first anchor through the anchor opening of the base and into the tissue of the patient. The first gear and the second gear rotate non-simultaneously.

30 Claims, 14 Drawing Sheets

(56) References Cited

U.S. PATENT DOCUMENTS

| | | |
|---|---|---|
| 2,737,954 A | 3/1956 | Knapp |
| 3,371,352 A | 3/1968 | Siposs |
| 3,569,660 A | 3/1971 | Houldcroft |
| 3,587,115 A | 6/1971 | Shiley |
| 3,596,660 A | 8/1971 | Melone |
| 3,667,081 A | 6/1972 | Burger |
| 3,688,764 A | 9/1972 | Reed |
| 3,731,352 A | 5/1973 | Okamoto |
| 3,840,018 A | 10/1974 | Heifetz |
| 3,958,562 A | 5/1976 | Hakim |
| 3,971,376 A | 7/1976 | Wichterle |
| 4,019,499 A | 4/1977 | Fitzgerald |
| 4,118,805 A | 10/1978 | Reimels |
| 4,151,835 A | 5/1979 | Copeland |
| 4,161,943 A | 7/1979 | Nogier |
| 4,164,943 A | 8/1979 | Hill |
| 4,190,040 A | 2/1980 | Schulte |
| 4,233,992 A | 11/1980 | Bisping |
| 4,265,252 A | 5/1981 | Chubbuck |
| 4,280,722 A | 7/1981 | Guptil |
| 4,413,985 A | 11/1983 | Wellner |
| 4,474,572 A | 10/1984 | McNaughton |
| 4,502,335 A | 3/1985 | Wamstad |
| 4,543,088 A | 9/1985 | Bootman |
| 4,557,722 A | 12/1985 | Harris |
| 4,569,675 A | 2/1986 | Prosl |
| 4,588,394 A | 5/1986 | Schulte |
| 4,592,339 A | 6/1986 | Kuzmak |
| 4,592,355 A | 6/1986 | Antebi |
| 4,634,427 A | 1/1987 | Hannula |
| 4,655,765 A | 4/1987 | Swift |
| 4,673,394 A | 6/1987 | Fenton |
| 4,692,146 A | 9/1987 | Hilger |
| 4,696,288 A | 9/1987 | Kuzmak |
| 4,704,103 A | 11/1987 | Stoeber |
| 4,710,174 A | 12/1987 | Moden |
| 4,738,657 A | 4/1988 | Hancock |
| 4,767,410 A | 8/1988 | Moden |
| 4,772,270 A | 9/1988 | Wiita |
| 4,778,452 A | 10/1988 | Moden |
| 4,781,680 A | 11/1988 | Redmond |
| 4,796,641 A | 1/1989 | Mills |
| 4,802,885 A | 2/1989 | Weeks |
| 4,832,054 A | 5/1989 | Bark |
| 4,840,615 A | 6/1989 | Hancock |
| 4,850,227 A | 7/1989 | Luettgen |
| 4,858,623 A | 8/1989 | Bradshaw |
| 4,861,341 A | 8/1989 | Woodburn |
| 4,881,939 A | 11/1989 | Newman |
| 4,886,501 A | 12/1989 | Johnston |
| 4,902,278 A | 2/1990 | Maget |
| 4,904,241 A | 2/1990 | Bark |
| 4,913,702 A | 4/1990 | Yum |
| 4,915,690 A | 4/1990 | Cone |
| 4,929,230 A | 5/1990 | Pfleger |
| 4,929,236 A | 5/1990 | Sampson |
| 4,966,588 A | 10/1990 | Rayman |
| 4,967,755 A | 11/1990 | Pohndorf |
| 4,978,338 A | 12/1990 | Melsky |
| 5,006,115 A | 4/1991 | McDonald |
| 5,013,298 A | 5/1991 | Moden |
| 5,026,344 A | 6/1991 | Dijkstra |
| 5,041,098 A | 8/1991 | Loiterman |
| 5,045,060 A | 9/1991 | Melsky |
| 5,074,868 A | 12/1991 | Kuzmak |
| 5,090,954 A | 2/1992 | Geary |
| 5,092,897 A | 3/1992 | Forte |
| 5,094,244 A | 3/1992 | Callahan |
| 5,108,377 A | 4/1992 | Cone |
| 5,125,408 A | 6/1992 | Basser |
| 5,133,753 A | 7/1992 | Bark |
| 5,137,529 A | 8/1992 | Watson |
| 5,147,483 A | 9/1992 | Melsky |
| 5,152,747 A | 10/1992 | Olivier |
| 5,167,638 A | 12/1992 | Felix |
| 5,185,003 A | 2/1993 | Brethauer |
| 5,207,644 A | 5/1993 | Strecker |
| 5,213,574 A | 5/1993 | Tucker |
| 5,226,429 A | 7/1993 | Kuzmak |
| 5,226,894 A | 7/1993 | Haber |
| 5,250,026 A | 10/1993 | Ehrlich |
| 5,273,537 A | 12/1993 | Haskvitz |
| 5,281,205 A | 1/1994 | McPherson |
| 5,284,479 A | 2/1994 | de Jong |
| 5,318,545 A | 6/1994 | Tucker |
| 5,336,194 A | 8/1994 | Polaschegg |
| 5,337,747 A | 8/1994 | Neftel |
| 5,360,407 A | 11/1994 | Leonard |
| 5,368,040 A | 11/1994 | Carney |
| 5,387,192 A | 2/1995 | Glantz |
| 5,391,164 A | 2/1995 | Giampapa |
| 5,449,368 A | 9/1995 | Kuzmak |
| 5,476,460 A | 12/1995 | Montalvo |
| 5,514,174 A | 5/1996 | Heil |
| 5,540,648 A | 7/1996 | Yoon |
| 5,556,388 A | 9/1996 | Johlin |
| 5,558,641 A | 9/1996 | Glantz |
| 5,562,617 A | 10/1996 | Finch |
| 5,571,104 A | 11/1996 | Li |
| 5,575,777 A | 11/1996 | Cover |
| 5,601,604 A | 2/1997 | Vincent |
| 5,637,102 A | 6/1997 | Tolkoff |
| 5,653,755 A | 8/1997 | Ledergerber |
| 5,658,298 A | 8/1997 | Vincent |
| 5,674,397 A | 10/1997 | Pawlak |
| 5,683,447 A | 11/1997 | Bush |
| 5,688,237 A | 11/1997 | Rozga |
| 5,695,490 A | 12/1997 | Flaherty |
| 5,716,342 A | 2/1998 | Dumbraveanu |
| 5,718,682 A | 2/1998 | Tucker |
| 5,722,957 A | 3/1998 | Steinbach |
| 5,748,200 A | 5/1998 | Funahashi |
| 5,810,735 A | 9/1998 | Halperin |
| 5,814,019 A | 9/1998 | Steinbach |
| 5,833,654 A | 11/1998 | Powers |
| 5,843,033 A | 12/1998 | Ropiak |
| RE36,176 E | 3/1999 | Kuzmak |
| 5,883,654 A | 3/1999 | Katsuyama |
| 5,902,598 A | 5/1999 | Chen |
| 5,906,596 A | 5/1999 | Tallarida |
| 5,910,149 A | 6/1999 | Kuzmak |
| 5,911,704 A | 6/1999 | Humes |
| 5,931,829 A | 8/1999 | Burbank |
| 5,932,460 A | 8/1999 | Mills |
| 5,935,083 A | 8/1999 | Williams |
| 5,938,669 A | 8/1999 | Klaiber |
| 5,951,512 A | 9/1999 | Dalton |
| 6,024,704 A | 2/2000 | Meador |
| 6,030,369 A | 2/2000 | Engelson |
| 6,039,712 A | 3/2000 | Fogarty |
| 6,074,341 A | 6/2000 | Anderson |
| 6,090,066 A | 7/2000 | Schnell |
| 6,098,405 A | 8/2000 | Miyata |
| 6,102,678 A | 8/2000 | Peclat |
| 6,102,922 A | 8/2000 | Jakobsson |
| 6,123,700 A | 9/2000 | Mills |
| 6,152,885 A | 11/2000 | Taepke |
| 6,171,252 B1 | 1/2001 | Roberts |
| 6,183,449 B1 | 2/2001 | Sibbitt |
| 6,213,973 B1 | 4/2001 | Eliasen |
| 6,221,024 B1 | 4/2001 | Miesel |
| 6,234,973 B1 | 5/2001 | Meador |
| 6,258,079 B1 | 7/2001 | Burbank |
| 6,264,676 B1 | 7/2001 | Gellman |
| 6,270,475 B1 | 8/2001 | Bestetti |
| 6,283,949 B1 | 9/2001 | Roorda |
| 6,321,124 B1 | 11/2001 | Cigaina |
| 6,349,740 B1 | 2/2002 | Cho |
| 6,432,040 B1 | 8/2002 | Meah |
| 6,450,946 B1 | 9/2002 | Forsell |
| 6,453,907 B1 | 9/2002 | Forsell |
| 6,454,699 B1 | 9/2002 | Forsell |
| 6,459,917 B1 | 10/2002 | Gowda |
| 6,461,293 B1 | 10/2002 | Forsell |

(56) References Cited

U.S. PATENT DOCUMENTS

| | | |
|---|---|---|
| 6,464,628 B1 | 10/2002 | Forsell |
| 6,470,213 B1 | 10/2002 | Alley |
| 6,470,892 B1 | 10/2002 | Forsell |
| 6,478,783 B1 | 11/2002 | Moorehead |
| 6,511,490 B2 | 1/2003 | Robert |
| 6,547,801 B1 | 4/2003 | Dargent |
| 6,572,587 B2 | 6/2003 | Lerman |
| 6,589,184 B2 | 7/2003 | Noren |
| 6,648,849 B2 | 11/2003 | Tenhuisen |
| 6,666,845 B2 | 12/2003 | Hooper |
| 6,689,100 B2 | 2/2004 | Connelly |
| 6,723,053 B2 | 4/2004 | Ackerman |
| 6,733,519 B2 | 5/2004 | Lashinski |
| 6,792,309 B1 | 9/2004 | Noren |
| 6,810,880 B1 | 11/2004 | Jennings |
| 6,813,964 B1 | 11/2004 | Clark |
| 6,860,857 B2 | 3/2005 | Noren |
| 6,915,162 B2 | 7/2005 | Noren |
| 6,921,267 B2 | 7/2005 | van Oostrom et al. |
| 6,929,631 B1 | 8/2005 | Brugger |
| 6,939,299 B1 | 9/2005 | Petersen |
| 6,953,444 B2 | 10/2005 | Rosenberg |
| 6,964,204 B2 | 11/2005 | Clark |
| 6,966,875 B1 | 11/2005 | Longobardi |
| 6,997,914 B2 | 2/2006 | Smith |
| 7,017,583 B2 | 3/2006 | Forsell |
| 7,020,531 B1 | 3/2006 | Colliou |
| 7,056,286 B2 | 6/2006 | Ravenscroft |
| 7,063,669 B2 | 6/2006 | Brawner |
| 7,073,387 B2 | 7/2006 | Zdeblick |
| 7,082,843 B2 | 8/2006 | Clark |
| 7,131,945 B2 | 11/2006 | Fink |
| 7,144,400 B2 | 12/2006 | Byrum |
| 7,149,587 B2 | 12/2006 | Wardle |
| 7,191,007 B2 | 3/2007 | Desai |
| 7,195,774 B2 | 3/2007 | Carvalho |
| 7,223,239 B2 | 5/2007 | Schulze |
| 7,226,419 B2 | 6/2007 | Lane |
| 7,261,003 B2 | 8/2007 | McDonald |
| 7,267,645 B2 | 9/2007 | Anderson |
| 7,282,023 B2 | 10/2007 | Frering |
| 7,311,716 B2 | 12/2007 | Byrum |
| 7,311,717 B2 | 12/2007 | Egle |
| 7,351,198 B2 | 4/2008 | Byrum |
| 7,351,226 B1 | 4/2008 | Herskowitz |
| 7,351,240 B2 | 4/2008 | Hassler |
| 7,353,747 B2 | 4/2008 | Swayze |
| 7,364,542 B2 | 4/2008 | Jambor |
| 7,367,937 B2 | 5/2008 | Jambor |
| 7,374,557 B2 | 5/2008 | Conlon |
| 7,374,565 B2 | 5/2008 | Hassler |
| 7,390,294 B2 | 6/2008 | Hassler |
| 7,413,547 B1 | 8/2008 | Lichtscheidl |
| 7,416,528 B2 | 8/2008 | Crawford |
| 7,437,951 B2 | 10/2008 | McDonald |
| 7,438,718 B2 | 10/2008 | Milliman |
| 7,445,614 B2 | 11/2008 | Bunodiere |
| 7,468,038 B2 | 12/2008 | Ye |
| 7,500,944 B2 | 3/2009 | Byrum |
| 7,510,530 B2 | 3/2009 | Hashimoto |
| 7,530,943 B2 | 5/2009 | Lechner |
| 7,553,298 B2 | 6/2009 | Hunt |
| 7,561,916 B2 | 7/2009 | Hunt |
| 7,580,746 B2 | 8/2009 | Gilkerson |
| 7,591,185 B1 | 9/2009 | Mothilal |
| 7,593,777 B2 | 9/2009 | Gerber |
| 7,634,319 B2 | 12/2009 | Schneider |
| 7,651,483 B2 | 1/2010 | Byrum |
| 7,658,196 B2 | 2/2010 | Ferreri |
| 7,699,770 B2 | 4/2010 | Hassler |
| 7,708,722 B2 | 5/2010 | Glenn |
| 7,762,998 B2 | 7/2010 | Birk |
| 7,762,999 B2 | 7/2010 | Byrum |
| 7,775,215 B2 | 8/2010 | Hassler |
| 7,775,966 B2 | 8/2010 | Dlugos |
| 7,811,275 B2 | 10/2010 | Birk |
| 7,850,660 B2 | 12/2010 | Uth |
| 7,862,546 B2 | 1/2011 | Conlon |
| 7,909,754 B2 | 3/2011 | Hassler |
| 7,909,804 B2 | 3/2011 | Stats |
| 8,007,474 B2 | 8/2011 | Uth |
| 2001/0052141 A1 | 12/2001 | Andersen |
| 2002/0013545 A1 | 1/2002 | Soltanpour |
| 2002/0058969 A1 | 5/2002 | Noren |
| 2002/0087147 A1 | 7/2002 | Hooper |
| 2002/0095181 A1 | 7/2002 | Beyar |
| 2002/0139208 A1 | 10/2002 | Yatskov |
| 2002/0198548 A1 | 12/2002 | Robert |
| 2003/0045800 A1 | 3/2003 | Noren |
| 2003/0045910 A1 | 3/2003 | Sorensen |
| 2003/0073880 A1 | 4/2003 | Polsky |
| 2003/0078506 A1 | 4/2003 | Noren |
| 2003/0139690 A1 | 7/2003 | Aebli |
| 2004/0064110 A1 | 4/2004 | Forsell |
| 2004/0065615 A1 | 4/2004 | Hooper |
| 2004/0068233 A1 | 4/2004 | DiMatteo |
| 2004/0082908 A1 | 4/2004 | Whitehurst |
| 2004/0111050 A1 | 6/2004 | Smedley |
| 2004/0204692 A1 | 10/2004 | Eliasen |
| 2004/0254536 A1 | 12/2004 | Conlon |
| 2004/0254537 A1 | 12/2004 | Conlon |
| 2004/0260229 A1 | 12/2004 | Meir |
| 2004/0260319 A1 | 12/2004 | Egle |
| 2004/0267288 A1 | 12/2004 | Byrum |
| 2004/0267291 A1 | 12/2004 | Byrum |
| 2004/0267292 A1 | 12/2004 | Byrum |
| 2004/0267293 A1 | 12/2004 | Byrum |
| 2004/0267377 A1 | 12/2004 | Egle |
| 2005/0010177 A1 | 1/2005 | Tsai |
| 2005/0049578 A1 | 3/2005 | Tu |
| 2005/0070875 A1 | 3/2005 | Kulessa |
| 2005/0070937 A1 | 3/2005 | Jambor |
| 2005/0085778 A1 | 4/2005 | Parks |
| 2005/0092093 A1 | 5/2005 | Kang |
| 2005/0131325 A1 | 6/2005 | Chen |
| 2005/0131352 A1 | 6/2005 | Conlon |
| 2005/0131383 A1 | 6/2005 | Chen |
| 2005/0148956 A1 | 7/2005 | Conlon |
| 2005/0149143 A1 | 7/2005 | Libbus |
| 2005/0209573 A1 | 9/2005 | Brugger |
| 2005/0240155 A1 | 10/2005 | Conlon |
| 2005/0240156 A1 | 10/2005 | Conlon |
| 2005/0267500 A1 | 12/2005 | Hassler |
| 2005/0277899 A1 | 12/2005 | Conlon |
| 2005/0283041 A1 | 12/2005 | Egle |
| 2005/0283118 A1 | 12/2005 | Uth |
| 2005/0283119 A1 | 12/2005 | Uth |
| 2006/0074439 A1 | 4/2006 | Garner |
| 2006/0122578 A1 | 6/2006 | Lord |
| 2006/0161186 A1 | 7/2006 | Hassler |
| 2006/0173423 A1 | 8/2006 | Conlon |
| 2006/0173424 A1 | 8/2006 | Conlon |
| 2006/0178647 A1 | 8/2006 | Stats |
| 2006/0178648 A1 | 8/2006 | Barron |
| 2006/0184141 A1 | 8/2006 | Smith |
| 2006/0189887 A1 | 8/2006 | Hassler |
| 2006/0189888 A1 | 8/2006 | Hassler |
| 2006/0190039 A1 | 8/2006 | Birk |
| 2006/0199997 A1 | 9/2006 | Hassler |
| 2006/0211912 A1 | 9/2006 | Dlugos |
| 2006/0211913 A1 | 9/2006 | Dlugos |
| 2006/0211914 A1 | 9/2006 | Hassler |
| 2006/0217668 A1 | 9/2006 | Schulze |
| 2006/0217673 A1 | 9/2006 | Schulze |
| 2006/0235445 A1 | 10/2006 | Birk |
| 2006/0235448 A1 | 10/2006 | Roslin |
| 2006/0247539 A1 | 11/2006 | Schugt |
| 2006/0266128 A1 | 11/2006 | Clark |
| 2006/0293625 A1 | 12/2006 | Hunt |
| 2006/0293626 A1 | 12/2006 | Byrum |
| 2006/0293627 A1 | 12/2006 | Byrum |
| 2006/0293628 A1 | 12/2006 | Hunt |
| 2007/0010790 A1 | 1/2007 | Byrum |
| 2007/0015954 A1 | 1/2007 | Dlugos |

(56) References Cited

U.S. PATENT DOCUMENTS

| | | |
|---|---|---|
| 2007/0015955 A1 | 1/2007 | Tsonton |
| 2007/0016231 A1 | 1/2007 | Jambor |
| 2007/0027356 A1 | 2/2007 | Ortiz |
| 2007/0038255 A1 | 2/2007 | Kieval |
| 2007/0060959 A1 | 3/2007 | Salo |
| 2007/0073250 A1 | 3/2007 | Schneiter |
| 2007/0078391 A1 | 4/2007 | Wortley |
| 2007/0088336 A1 | 4/2007 | Dalton |
| 2007/0088391 A1 | 4/2007 | McAlexander |
| 2007/0129765 A1 | 6/2007 | Gilkerson |
| 2007/0135758 A1 | 6/2007 | Childers |
| 2007/0149947 A1 | 6/2007 | Byrum |
| 2007/0156013 A1 | 7/2007 | Birk |
| 2007/0158769 A1 | 7/2007 | You |
| 2007/0161958 A1 | 7/2007 | Glenn |
| 2007/0167672 A1 | 7/2007 | Dlugos |
| 2007/0173685 A1 | 7/2007 | Jambor |
| 2007/0185462 A1 | 8/2007 | Byrum |
| 2007/0191717 A1 | 8/2007 | Rosen |
| 2007/0205384 A1 | 9/2007 | Kurosawa |
| 2007/0208313 A1 | 9/2007 | Conlon |
| 2007/0213837 A1 | 9/2007 | Ferreri |
| 2007/0219510 A1 | 9/2007 | Zinn |
| 2007/0235083 A1 | 10/2007 | Dlugos |
| 2007/0250086 A1 | 10/2007 | Wiley |
| 2007/0255165 A1 | 11/2007 | Uesugi |
| 2007/0255234 A1 | 11/2007 | Haase |
| 2007/0265666 A1 | 11/2007 | Roberts |
| 2007/0282196 A1 | 12/2007 | Birk |
| 2007/0293829 A1 | 12/2007 | Conlon |
| 2008/0009680 A1 | 1/2008 | Hassler |
| 2008/0015406 A1 | 1/2008 | Dlugos |
| 2008/0039772 A1 | 2/2008 | Chantriaux |
| 2008/0058632 A1 | 3/2008 | Tai |
| 2008/0097496 A1 | 4/2008 | Chang |
| 2008/0114308 A1 | 5/2008 | di Palma et al. |
| 2008/0119798 A1 | 5/2008 | Chantriaux |
| 2008/0243093 A1 | 10/2008 | Kalpin |
| 2008/0249806 A1 | 10/2008 | Dlugos |
| 2008/0250340 A1 | 10/2008 | Dlugos |
| 2008/0250341 A1 | 10/2008 | Dlugos |
| 2008/0255403 A1 | 10/2008 | Voegele |
| 2008/0255414 A1 | 10/2008 | Voegele |
| 2008/0255425 A1 | 10/2008 | Voegele |
| 2008/0255459 A1 | 10/2008 | Voegele |
| 2008/0255537 A1 | 10/2008 | Voegele |
| 2008/0281412 A1 | 11/2008 | Smith |
| 2008/0287969 A1 | 11/2008 | Tsonton |
| 2008/0287974 A1 | 11/2008 | Widenhouse |
| 2008/0312553 A1 | 12/2008 | Timmons |
| 2008/0319435 A1 | 12/2008 | Rioux |
| 2009/0018608 A1 | 1/2009 | Schwartz |
| 2009/0048524 A1 | 2/2009 | Wildau |
| 2009/0054914 A1 | 2/2009 | Lechner |
| 2009/0062825 A1 | 3/2009 | Pool |
| 2009/0071258 A1 | 3/2009 | Kouda |
| 2009/0076466 A1 | 3/2009 | Quebbemann |
| 2009/0082757 A1 | 3/2009 | Rogers |
| 2009/0082793 A1 | 3/2009 | Birk |
| 2009/0093768 A1 | 4/2009 | Conlon |
| 2009/0099538 A1 | 4/2009 | Paganon |
| 2009/0105735 A1 | 4/2009 | Stam |
| 2009/0112308 A1 | 4/2009 | Kassem |
| 2009/0118572 A1 | 5/2009 | Lechner |
| 2009/0149874 A1 | 6/2009 | Ortiz |
| 2009/0157106 A1 | 6/2009 | Marcotte |
| 2009/0157107 A1 | 6/2009 | Kierath |
| 2009/0157113 A1 | 6/2009 | Marcotte |
| 2009/0171375 A1 | 7/2009 | Coe |
| 2009/0171378 A1 | 7/2009 | Coe |
| 2009/0171379 A1 | 7/2009 | Coe |
| 2009/0192404 A1 | 7/2009 | Ortiz |
| 2009/0192415 A1 | 7/2009 | Ortiz |
| 2009/0192533 A1 | 7/2009 | Dlugos |
| 2009/0192534 A1 | 7/2009 | Ortiz |
| 2009/0192541 A1 | 7/2009 | Ortiz |
| 2009/0198261 A1 | 8/2009 | Schweikert |
| 2009/0202387 A1 | 8/2009 | Dlugos |
| 2009/0204131 A1 | 8/2009 | Ortiz |
| 2009/0204132 A1 | 8/2009 | Ortiz |
| 2009/0209995 A1 | 8/2009 | Byrum |
| 2009/0216255 A1 | 8/2009 | Coe |
| 2009/0221974 A1 | 9/2009 | Paganon |
| 2009/0222031 A1 | 9/2009 | Axelsson |
| 2009/0222065 A1 | 9/2009 | Dlugos |
| 2009/0227862 A1 | 9/2009 | Smith |
| 2009/0228028 A1 | 9/2009 | Coe |
| 2009/0228072 A1 | 9/2009 | Coe |
| 2009/0248125 A1 | 10/2009 | Brostrom |
| 2009/0248126 A1 | 10/2009 | Nippoldt |
| 2009/0254052 A1 | 10/2009 | Birk |
| 2009/0259190 A1 | 10/2009 | Birk |
| 2009/0259191 A1 | 10/2009 | Birk |
| 2009/0259231 A1 | 10/2009 | Birk |
| 2009/0264901 A1* | 10/2009 | Franklin et al. ............ 606/139 |
| 2009/0270904 A1 | 10/2009 | Birk |
| 2009/0299216 A1 | 12/2009 | Chen |
| 2009/0299672 A1 | 12/2009 | Zhang |
| 2009/0306462 A1 | 12/2009 | Lechner |
| 2009/0308169 A1 | 12/2009 | Mothilal |
| 2010/0087843 A1 | 4/2010 | Bertolote |
| 2010/0100079 A1 | 4/2010 | Berkcan |
| 2010/0114149 A1 | 5/2010 | Albrecht |
| 2010/0130941 A1 | 5/2010 | Conlon |
| 2010/0152532 A1 | 6/2010 | Marcotte |
| 2010/0191271 A1 | 7/2010 | Lau |
| 2010/0211085 A1 | 8/2010 | Uth |
| 2010/0217198 A1 | 8/2010 | Franklin |
| 2010/0217199 A1 | 8/2010 | Uth |
| 2010/0217200 A1 | 8/2010 | Uth |
| 2010/0228080 A1 | 9/2010 | Tavori |
| 2010/0234808 A1 | 9/2010 | Uth |
| 2011/0054407 A1 | 3/2011 | Olroyd |
| 2011/0082426 A1 | 4/2011 | Conlon |
| 2012/0041258 A1* | 2/2012 | Jacobs et al. ............ 600/37 |

FOREIGN PATENT DOCUMENTS

| | | |
|---|---|---|
| DE | 3927001 | 2/1991 |
| DE | 4211045 | 10/1993 |
| DE | 19745654 | 4/1999 |
| DE | 19751791 | 5/1999 |
| EP | 0343910 A2 | 11/1989 |
| EP | 0611561 | 8/1994 |
| EP | 0858814 | 8/1998 |
| EP | 0867197 | 9/1998 |
| EP | 1057457 | 12/2000 |
| EP | 1346753 | 9/2003 |
| EP | 1396242 A1 | 3/2004 |
| EP | 1396243 A1 | 3/2004 |
| EP | 1488824 A1 | 12/2004 |
| EP | 1543861 A1 | 6/2005 |
| EP | 1547643 | 6/2005 |
| EP | 1591140 A1 | 11/2005 |
| EP | 1736194 A1 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 A1 | 6/2009 |
| EP | 2095798 | 9/2009 |
| FR | 2740977 | 5/1997 |
| FR | 2797181 A1 | 2/2001 |
| FR | 2823663 A1 | 10/2002 |
| FR | 2851168 | 8/2004 |
| FR | 2855744 A1 | 12/2004 |
| FR | 2916980 | 12/2008 |
| JP | 2119877 | 5/1990 |
| JP | 8107934 | 4/1996 |
| SU | 1823791 | 6/1991 |
| WO | 9220519 A1 | 11/1992 |

(56) References Cited

FOREIGN PATENT DOCUMENTS

| WO | 9422520 | 10/1994 |
|---|---|---|
| WO | 9640357 | 12/1996 |
| WO | 9701370 | 1/1997 |
| WO | 9920338 | 4/1999 |
| WO | 9926543 | 6/1999 |
| WO | 9934859 | 7/1999 |
| WO | 0015158 A1 | 3/2000 |
| WO | 0033901 | 6/2000 |
| WO | 0110359 A1 | 2/2001 |
| WO | 0149245 A2 | 7/2001 |
| WO | 0180926 | 11/2001 |
| WO | 0195813 A1 | 12/2001 |
| WO | 0210667 A2 | 2/2002 |
| WO | 02074381 | 9/2002 |
| WO | 03105732 A1 | 12/2003 |
| WO | 2004016971 | 2/2004 |
| WO | 2005037055 A2 | 4/2005 |
| WO | 2005072627 A1 | 8/2005 |
| WO | 2006021695 | 3/2006 |
| WO | 2009007526 | 1/2009 |
| WO | 2009129474 A1 | 10/2009 |

OTHER PUBLICATIONS

Geim AK. et al.; 'Microfabricated Adhesive Mimicking Gecko Foot-Hair'; Nature Materials Abstract only; vol. 2; No. 7; 2003.

Yamagami, Takuji; 'Technical Developments; Use of Targeting Guide Wire in Left Subclavian Puncture During Percutaneous Implantation of Port-Catheter Systems Using the Catheter Tip Fixation Method' European Radiology; vol. 13; pp. 863-866; 2003.

Yurdumakan B., et al.; 'Synthetic Gecko Foot-Hairs from Multiwalled Carbon Nanotubes'; The Royal Society of Chemistry; p. 3799-3801; 2005.

* cited by examiner

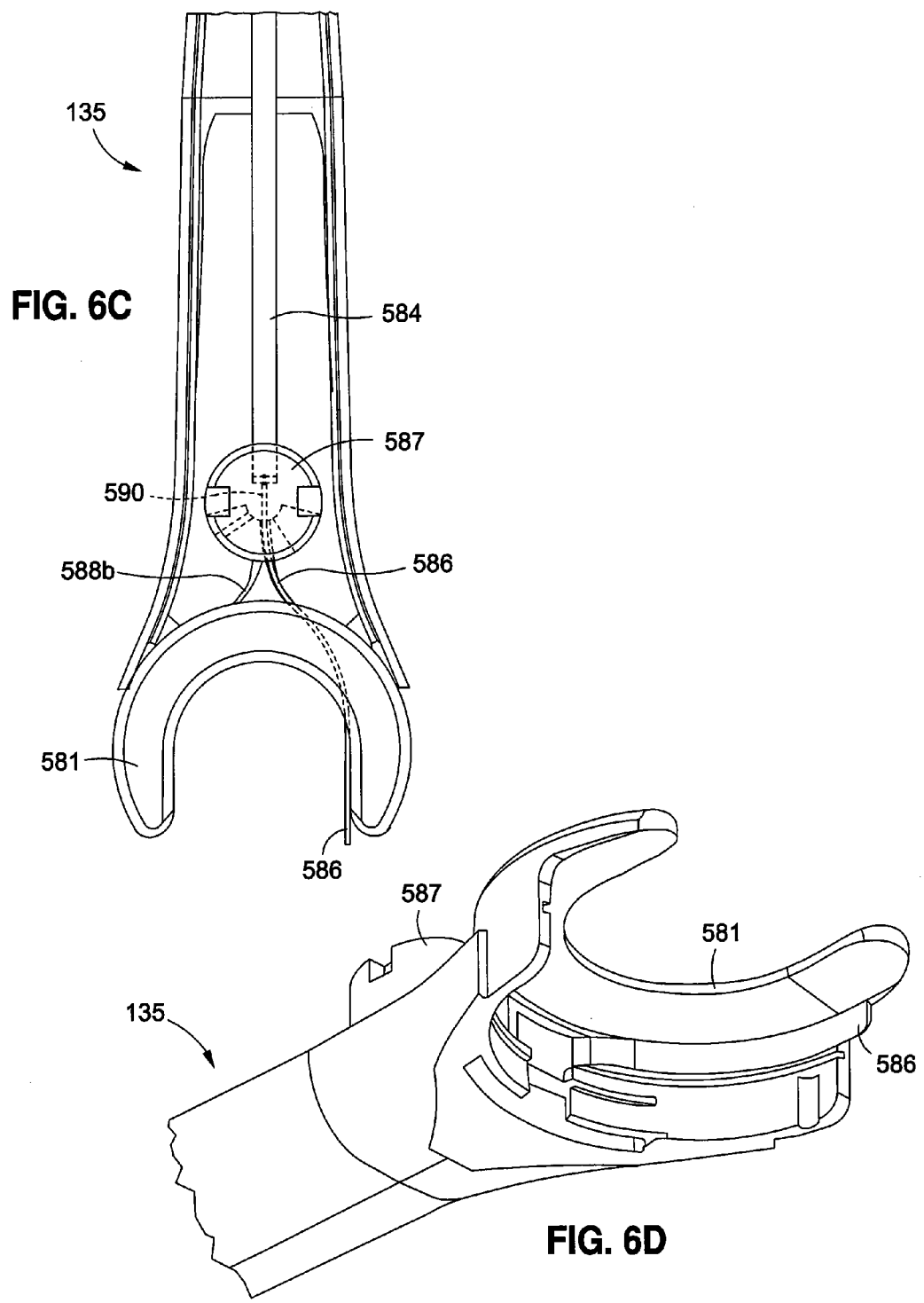

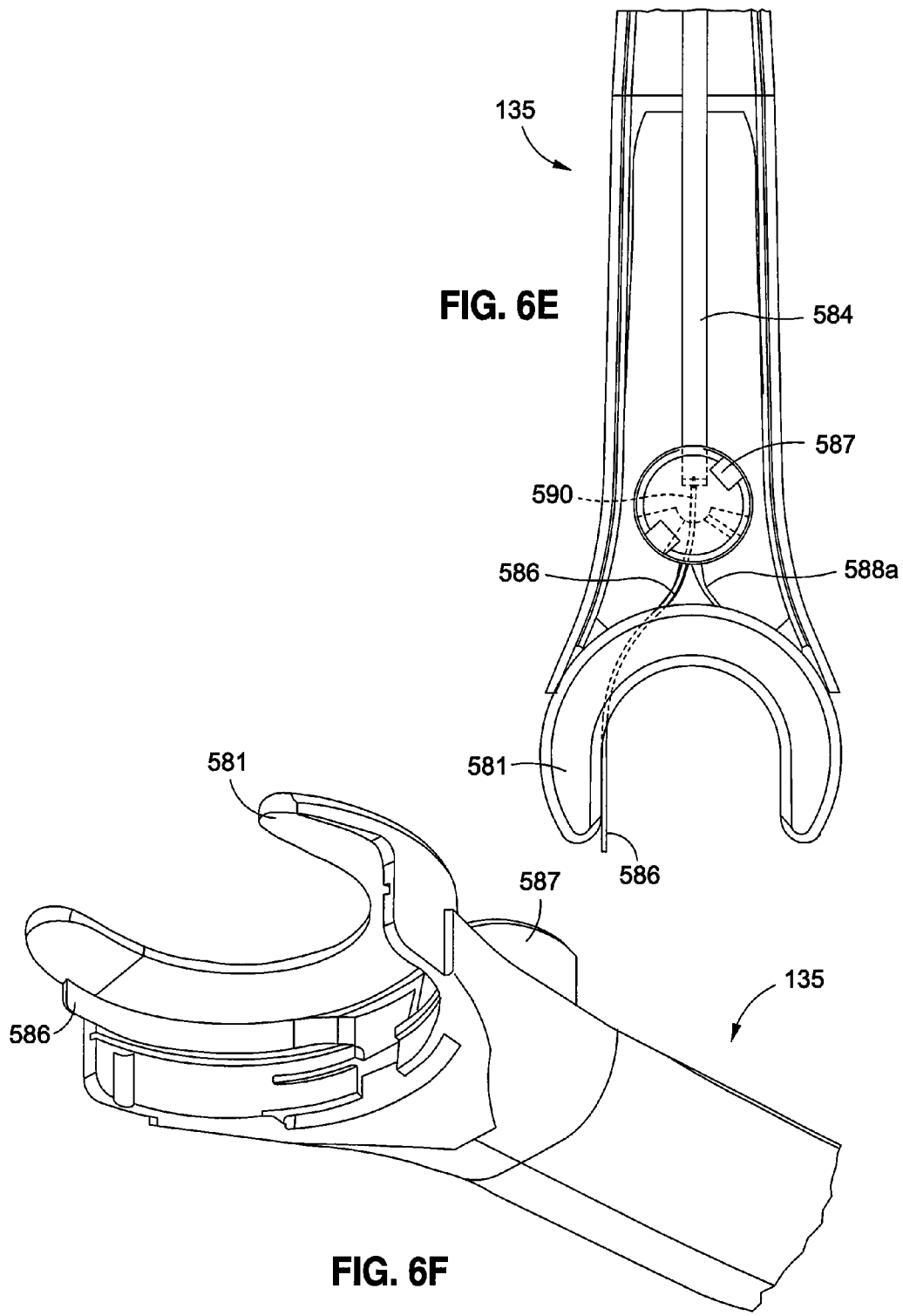

IMPLANTABLE ACCESS PORT SYSTEM

CROSS REFERENCE TO RELATED APPLICATIONS

This application is a continuation of U.S. patent application Ser. No. 12/881,460, filed Sep. 14, 2010, the contents of which is incorporated herein by reference.

BACKGROUND

1. Field

The present invention relates generally to implantable access ports and attachment mechanisms or systems for attaching the implantable access ports to a patient. More specifically, the present invention relates to implantable access ports with independent moving gears for the anchors, and related actuation devices.

2. Description of the Related Art

Implantable medical devices for performing therapeutic functions for a patient are well known. Such devices include pace makers, vascular access ports, injection ports (such as those used with gastric banding devices) and gastric pacing devices. Such devices are attached to a human, typically subcutaneously, in an appropriate place in order to function properly. It is desirable that the procedure to implant such devices be quick, easy, efficient, and require as small of an incision as possible.

A suture (also known as stitches) is typically used by doctors to hold skin, internal organs, blood vessels and all other tissues of the human body together after they have been severed by injury, incision or surgery. Suturing is both time consuming and inconvenient. Surgical fasteners, such as staples, clips, clamps, bands, tacks, or other wound or incision closure devices, have been used in surgical procedures to eliminate the need for suturing. Surgical fasteners are commonly used in surgical procedures to allow a surgeon to fasten, secure, and/or repair bodily tissue. In these applications, the surgeon often uses a fastener implanting device loaded with one or more surgical fasteners to accomplish in a few seconds what would have taken many minutes to perform by suturing. This reduction in operating time reduces blood loss and trauma to the patient.

Typically, such surgical fasteners have been used mainly for the closure of incisions or wounds, or to fasten tissues together. A surgical fastener that can be used with a number of different types of implantable medical devices would be beneficial for surgeons. Currently, surgical systems that incorporate surgical fasteners often use extremely specialized devices that may be unnecessarily complicated and are unsuitable for adaptation to other applications.

As a result, the majority of implantable medical devices are secured with sutures. For example, when inserting a gastric band and an associated access port, the associated access port may be sutured into place with 3 to 5 sutures against the rectus muscle sheath. Such placement of the sutures is often challenging because the associated access port is placed below several inches of bodily tissue (e.g., fat), and suturing the associated access port often takes as long as placing the gastric band itself. An improved fastening device would allow easy, one-step attachment with security equivalent to the sutured medical device.

One conventional method for fastening an implantable access port to the patient includes an external pistol-like applying means. The external pistol may include a trigger having geared teeth, a gear which meshes with the geared teeth, and a spring. The external pistol attaches to the implantable access port and tightens a fastener into the tissue of the patient upon pressing of the trigger. After attachment, the external pistol is removed from the implantable access port. Examples of similar methods may be found in European Patent Application Pub. No. 1736194 and U.S. Patent Application Pub. No. 2005/0283118.

Another conventional method for fastening an implantable access port includes fasteners extending from the housing of the implantable access port. In a self-attaching method, the implantable access port may be self-attached upon the surgeon applying a distal force to the access port housing, causing the fasteners to penetrate the tissue, engaging the tissue to hold the access port in place. Examples of similar methods may be found in U.S. Patent Application Pub. Nos. 2004/0254537, 2006/0190039, 2006/0235445, and 2009/0259190. In an electronic method, the fasteners may be electronically switched between a deployed position and an un-deployed position using an actuator.

European Patent Application Pub. No. 1543861 and U.S. Patent Application Pub. No. 2005/0131352 disclose an injection port that may be implanted using separate fasteners that are not part of the port prior to implantation. These fasteners are inserted one at a time using a tool. Thus, the tool is repositioned prior to implanting each fastener, which may lead to inefficiencies and inaccuracies in the implantation. U.S. Pat. No. 7,374,557 also discloses individually inserted fasteners.

The present invention overcomes at least some of the drawbacks of these conventional medical devices and methods.

SUMMARY

Generally described herein are implantable access ports and related actuation devices. The apparatus, systems and methods described herein provide relatively easy attachment capabilities of the implantable access ports to bodily tissue.

In one example embodiment, an implantable injection port comprises a base with a first anchor opening. A first gear is coupled to the base and is rotatable about a first axis, and a first anchor is coupled to the first gear. A second gear is coupled to the base and is rotatable about a second axis, and a second anchor is coupled to the second gear. The first gear has a first plurality of gear teeth, and the second gear has a second plurality of gear teeth.

A top portion of the injection port is spaced apart from the base of the port and has a first plurality of top teeth that engage with the first plurality of gear teeth on the first gear. This engagement occurs prior to rotation of the second gear. The top portion rotates, which causes rotation of the first gear, which in turn causes movement of the first anchor through the anchor opening of the base and into the tissue of the patient. The first gear rotates about the first axis independently of the second gear rotating about a second axis and prior to the second anchor being implanted in the tissue of the patient. Thus, the first gear and the second gear rotate non-simultaneously.

In another embodiment of the present invention, an actuation device for attaching an implantable injection port comprises a head for coupling to the implantable injection port. A first drive band is coupled to a trigger of the actuation device, and a second drive band is coupled to the first drive band for translating motion from the trigger of the actuation device to the second drive band. The second drive band interfaces with a top portion of the implantable injection port to facilitate deploying an anchor of the implantable injection port into the tissue of the patient. A switch on a housing of the actuation device is operable to direct the second drive band to rotate the top portion of the implantable injection port in an implanting direction or a retracting direction.

Further, in accordance with an embodiment, a method for implanting an implantable injection port comprises coupling a gripping portion of an actuation device to a top portion of the implantable injection port. A trigger of the actuation device is depressed when a switch in the actuation device is located in an implanting orientation. A vertical drive band is then directed through the switch to contact the top portion of the implantable injection port and rotate the top portion in an implanting direction.

At a first time, a first anchor coupled to a first gear is implanted into the tissue of the patient in response to a first set of top teeth causing the first gear to rotate. At a second time, a second anchor coupled to a second gear is implanted into the tissue of the patient in response to the first set of top teeth or a second set of top teeth causing the second gear to rotate.

BRIEF DESCRIPTION OF THE DRAWINGS

The features, objects, and advantages of the invention will become more apparent from the detailed description set forth below when taken in conjunction with the drawings, wherein:

FIG. 6C illustrates a sectional view of a gripping end of an applier tool showing a vertical drive band in an implanting orientation according to an embodiment of the present invention.

FIG. 6D illustrates a perspective view of a gripping end of an applier tool showing a vertical drive band in an implanting orientation according to an embodiment of the present invention.

FIG. 6E illustrates a sectional view of a gripping end of an applier tool showing a vertical drive band in a removal orientation according to an embodiment of the present invention.

FIG. 6F illustrates a perspective view of a gripping end of an applier tool showing a vertical drive band in a removal orientation according to an embodiment of the present invention.

DETAILED DESCRIPTION

Apparatus, systems and methods that implement the embodiments of the various features of the present invention will now be described with reference to the drawings. The drawings and the associated descriptions are provided to illustrate some embodiments of the present invention and not to limit the scope of the present invention. Throughout the drawings, reference numbers are re-used to indicate correspondence between referenced elements.

A system is disclosed having a port (e.g., an implantable access port or an implantable injection port) that is securely fastened to bodily tissue of a human or a patient. The port is used to fill and remove fluid from an inflatable portion of a band (e.g., a gastric band) via a catheter attached between the port and the inflatable portion of the band. One or more anchors (e.g., four anchors) of the port may be subcutaneously and securely attached to the bodily tissue of the human by rotating one or more mating components (e.g., an applier, an axle, a cap, a gear, etc.). The one or more mating components provide a continually secure attachment of the one or more anchors to the bodily tissue of the patient after surgery.

Figure 1:
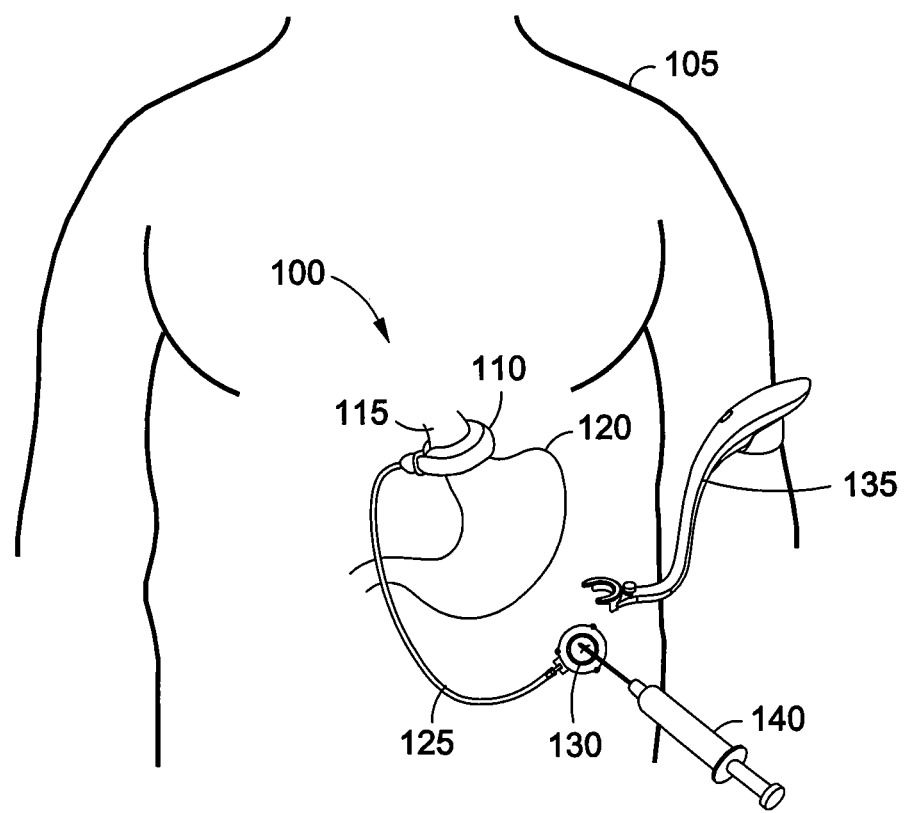
FIG. 1 illustrates a patient with an implantable injection port and an applier tool according to an embodiment of the present invention.

FIG. 1 is a simplified partial front view of a human body 105 with a food intake restriction system, such as an implantable gastric banding system 100 having a band 110, a port 130 and an applier 135 according to an embodiment of the present invention. The gastric banding system 100 is used to treat obesity and to attach to a tissue of a patient. The band 110 may be a gastric band, such as the Lap-Band®, and may be adjustable, implantable, inflatable and positioned around or near the upper portion of a stomach 120 of a human 105. Generally, the band 110 is placed about the fundus, or esophageal junction, of a patient's upper stomach forming a stoma that restricts the food's passage into a lower portion of the stomach. The band 110 may include an inflatable portion (e.g., a cavity) made of silicone rubber, or another type of biocompatible material, that inflates or expands inward to constrict the stoma (stomach inlet) when filled with a fluid (e.g., saline) from the tubing, such as a catheter 125. Alternatively, a mechanical device or a combination hydraulic/mechanical device may be coupled to the band 110 to constrict the stoma. When the stoma is of an appropriate size that is restricted by the band 110, food held in the upper portion of the stomach may provide a feeling of satiety or fullness that discourages overeating.

The port 130 may be implanted in a body region accessible for needle injections from a syringe 140 and/or for receiving telemetry communication signals. The port 130 is a medical device that may be referred to as an access port, an injection port, an implantable access device/port or a housing. The port 130 fluidly communicates with the inflatable portion of the band 110 via the catheter 125.

A medical professional (e.g., doctor, health care provider, nurse, surgeon, technician, etc.) may position and temporarily or permanently implant the port 130 inside the body of the human 105 in order to perform adjustments of the food intake restriction or stoma created by the band 110. The medical professional, for example, may implant the port 130 in the lateral, subcostal region of the human's abdomen under the skin and layers of fatty tissue, or on or near the sternum of the human 105. Also, any other suitable attachment areas or port sites may be used.

The applier 135 may be used to secure the port 130 to the human 105, as depression of an applier trigger facilitates rotation of a portion of the port 130 to secure anchors of the port 130 into bodily tissue of the human 105. In particular, the anchors may be moved from an undeployed position to a deployed position. The applier 135 may be a tool such as a delivery tool.

Figure 2A:
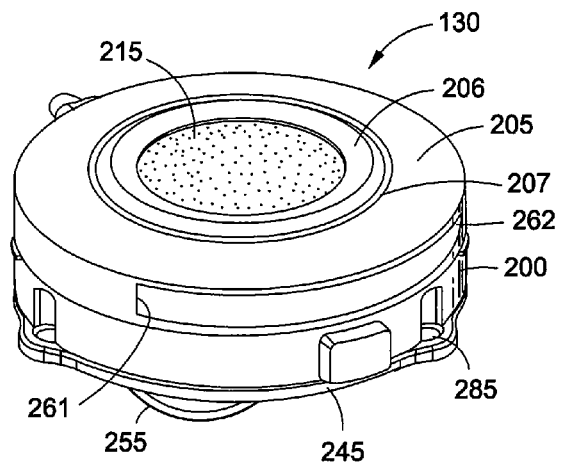
FIG. 2A illustrates a perspective view of an implantable injection port according to an embodiment of the present invention.
Figure 2B:
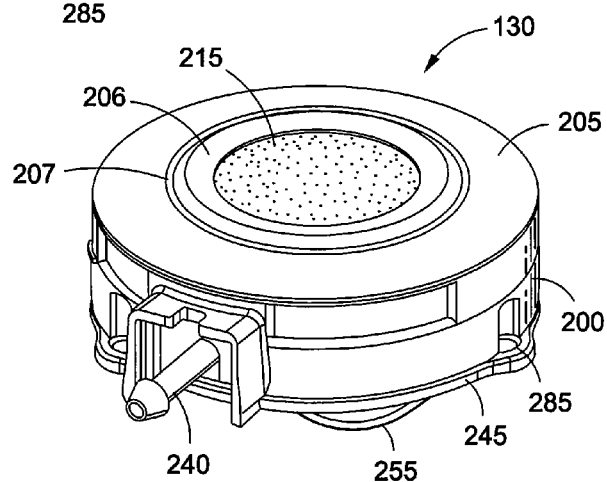
FIG. 2B illustrates a perspective view of an implantable injection port showing a stem according to an embodiment of the present invention.
Figure 3:
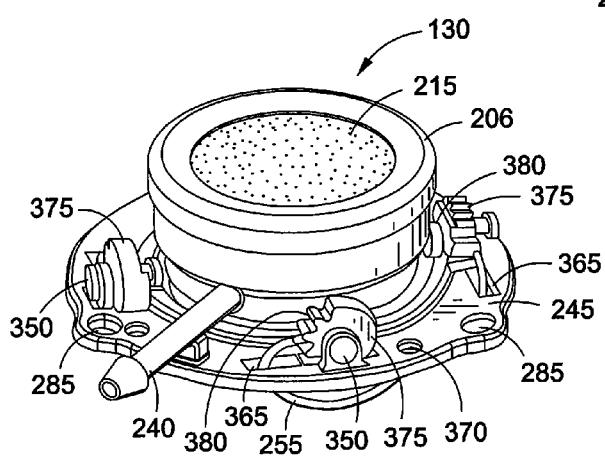
FIG. 3 illustrates a perspective view of an implantable injection port without a port housing according to an embodiment of the present invention.
Figure 4:
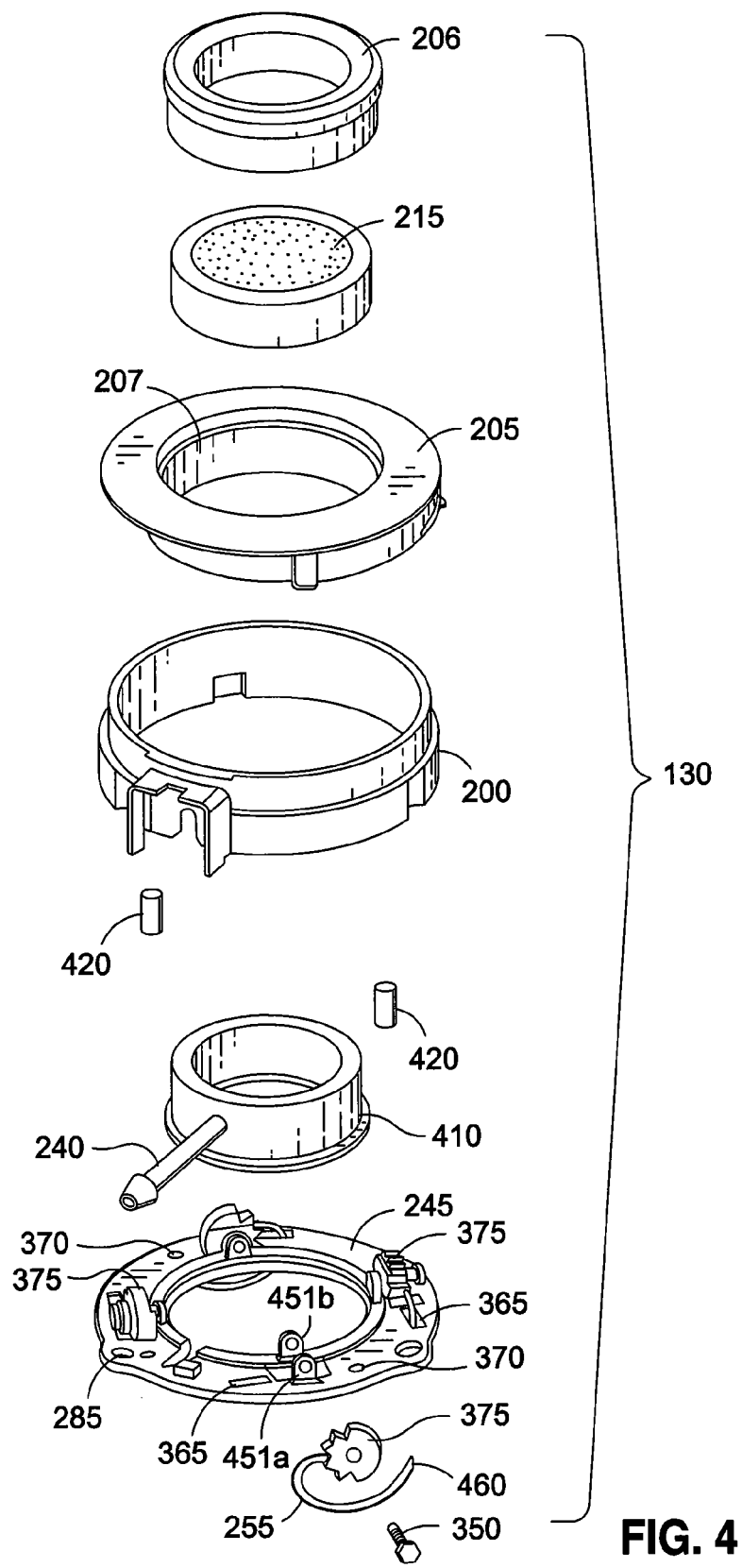
FIG. 4 illustrates an exploded, perspective view of an implantable injection port according to an embodiment of the present invention.

FIGS. 2A-2B are perspective views of the port 130 according to an embodiment of the present invention, illustrating a top portion 205 that connects to or meshes with the applier 135. FIG. 3 is a perspective view of the port 130 of FIGS. 2A-2B with the top portion 205 removed to show a set of gears 375 with gear teeth 380 coupled to anchors 255. FIG. 4 is an exploded, perspective view showing the different parts of the port 130 of FIG. 2 according to an embodiment of the present invention.

Referring to FIGS. 2A-4, the port 130 is configured to receive fluid from the syringe 140 for movement into the inflatable portion of the band 110. The port 130 includes the top portion 205 and the reservoir 410. The reservoir 410 contains an interior space for holding the fluid. The reservoir 410 may be an internal titanium port reservoir or a port without the top portion 205. As shown in FIG. 4, the reservoir 410 is formed in the shape of a cylinder.

The top portion 205 may be a drive cap, a port cap, a rotating cap, a top cap or a top outer ring. The top portion 205 may have a lip 261 that facilitates rotating the top portion 205 to implant the port 130, and a lip 262 that facilitates rotating the top portion 205 to remove the port 130, as discussed further below. The top portion 205 may be attached to or may be integrally formed with an inner ring 206. The inner ring 206 may also be referred to as a flange. Alternatively, the top portion 205 may include the inner ring 206.

The top portion 205 may have a center opening 207. The center opening 207 allows the inner ring 206 to fit therein. In addition, a septum 215 (e.g., a needle penetrable septum) may be located or positioned within the inner ring 206 and/or the center opening 207 of the top portion 205. The inner ring 206 and/or the septum 215 may be attached to the reservoir 410. The top portion 205 may rotate without rotating the inner ring 206 and/or the septum 215. That is, the inner ring 206 and/or the septum 215 may be permanently attached or fixedly attached to the reservoir 410. In one embodiment, the top portion 205 is moveably or rotatably attached to the inner ring 206.

As an example, the syringe 140 may be used to pierce the septum 215, thus allowing the fluid in the syringe 140 to pass into the reservoir 410 and then ultimately through the catheter 125 and into the inflatable portion of the band 110. Also, the syringe 140 may be used to remove fluid from the reservoir 410, which causes the fluid in the inflatable portion of the band 110 to be removed therefrom. The septum 215 may be made of any suitable needle penetrable material, for example, a self sealing, needle penetrable material.

The port 130 has a base 245, one or more axles 350, one or more axle holders 451, one or more gears 375 and one or more anchors 255. The anchors 255 and the gears 375 may be formed as one piece, or as separate pieces that may be joined together. The base 245 may also be referred to as a port base, a bottom base, a bottom cap, a bottom ring or a bottom portion. The base 245 may lie along a plane that is substantially parallel to the plane defined by the top portion 205. The reservoir 410 is fixedly attached to the base 245 and does not move with the rotation of the top portion 205.

The base 245 includes one or more anchor openings 365 and one or more tip openings 370. As an example, the one or more anchor openings 365 may be formed in the shape of a rectangle and the one or more tip openings 370 may be formed in the shape of a circle. The anchors 255 may be locked into place in the base 245 after deployment using a flat interference locating feature, for example, in the anchor openings 365. A housing 200 is disposed about the reservoir 410, between the base 245 and the top cover 250.

The axle holder 451 is attached to or integrated with the base 245. The axle holder 451 may include two pylons 451a, 451b, each having a hole for the axle 350 to pass therethrough (see FIG. 4). The two pylons 451a, 451b are positioned adjacent to and on opposite sides of the anchor opening 365. The anchor 255 and the gear 375 also have openings that allow for the axle 350 to pass therethrough. The component with the anchor 255 and the gear 375 fit between the two pylons 451a, 451b. The axle 350 passes through the holes of the pylori 451a, the anchor 255, the gear 375, and the pylori 451b and is positioned therein. The rotational movement of the gear 375 causes a similar circular or rotational movement of the anchor 255.

The axle 350 may rotate circularly when force is applied thereon. The axle 350 may also be referred to as a center pin. The gear 375, attached to the axle 350, may rotate in unison with and/or about the axle 350.

The base 245 may be moveably attached to the top portion 205 by the reservoir 410. A stem 240 is attached to the reservoir 410 for moving the fluid from the port 130 to the band 110. The stem 240 may include a strain relief element which locks into a housing 200 and protects the catheter 125 from folding, kinking, rotating, or torquing when the catheter 125 is connected to the reservoir 410. The housing 200 may also be referred to as a port housing. The housing 200 surrounds the port 130 and covers the components therein.

A radiopaque marker 420 is a type of locator element on the port 130 that is visible under an x-ray. The radiopaque marker 420 may be secured in the housing 200 so as not to hide the radiopaque marker 420. The radiopaque markers 420 can be used to facilitate identification of the type of gastric band or other useful information to be identified by the x-ray image of the port 130, for example, by using varied configurations, sizes or shapes of the radiopaque marker 420.

In accordance with an embodiment, the housing 200, the base 245, the top portion 205, and the gears 375 may be made of implantable grade plastic. Further, the anchors 255, the axels 250, and the radiopaque markers 420 may be made of implantable grade metal. Additionally, the reservoir 410 may be made of implantable grade titanium, and the septum 215 may be made of implantable silicone. It should be understood that other materials are contemplated within the scope of the present invention, and the above are only representative materials according to an embodiment.

In an embodiment, the port 130 may be assembled as follows. The anchor 255 and the gear 375 structure and/or assembly is inserted between the pylons 451a, 451b, and the anchor assembly is rotatably secured to the pylons 451a, 451b with the axle 250. The axle head may be configured to sit flush with the pylori 451a. The above process is repeated until all of the anchors 255 and the gears 375 are assembled. In an embodiment, the anchors 255 are assembled in a fully deployed position. The reservoir 410 and the stem 240 subassembly are then inserted into the base 245, for example, by leading with the stem 240 and coming in from the bottom of the base 245. The stem 240 may be aligned over a supporting block on the base 245. Then, the septum 215 may be inserted into the reservoir 410. The housing 200 is then aligned with the radiopaque markers 420 and inserted, following which the top portion 205 is aligned and inserted. The inner ring 206 or a port cover may then be inserted and pressed into place around the septum 215 and within the top portion 205.

Figure 5A:
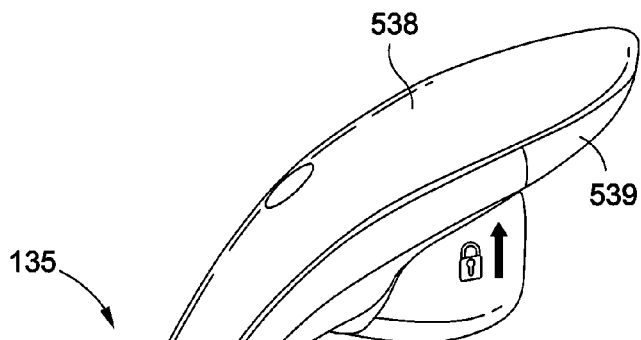
FIG. 5A illustrates a perspective view of an applier tool according to an embodiment of the present invention.
Figure 5B:
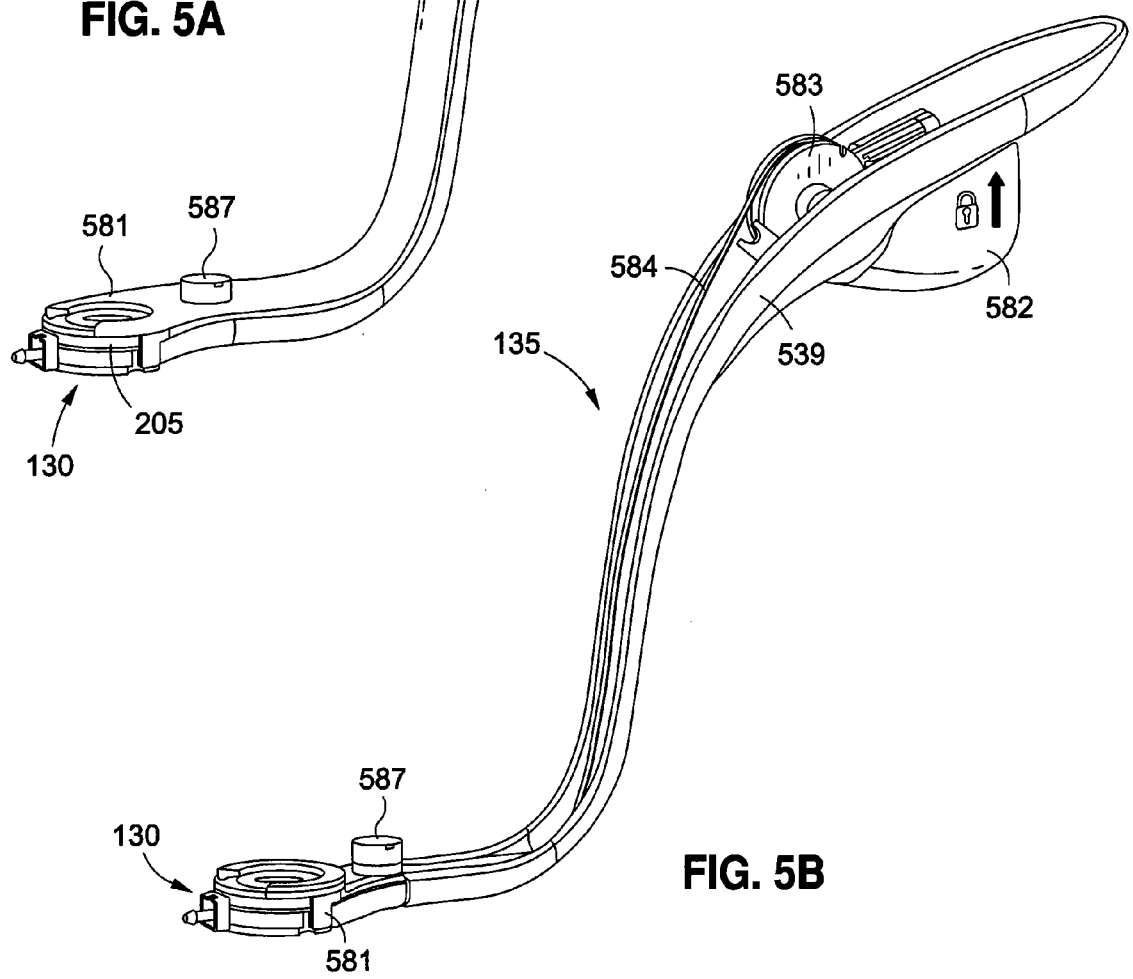
FIG. 5B illustrates a perspective view of an applier tool without a housing cover according to an embodiment of the present invention.
Figure 5C:
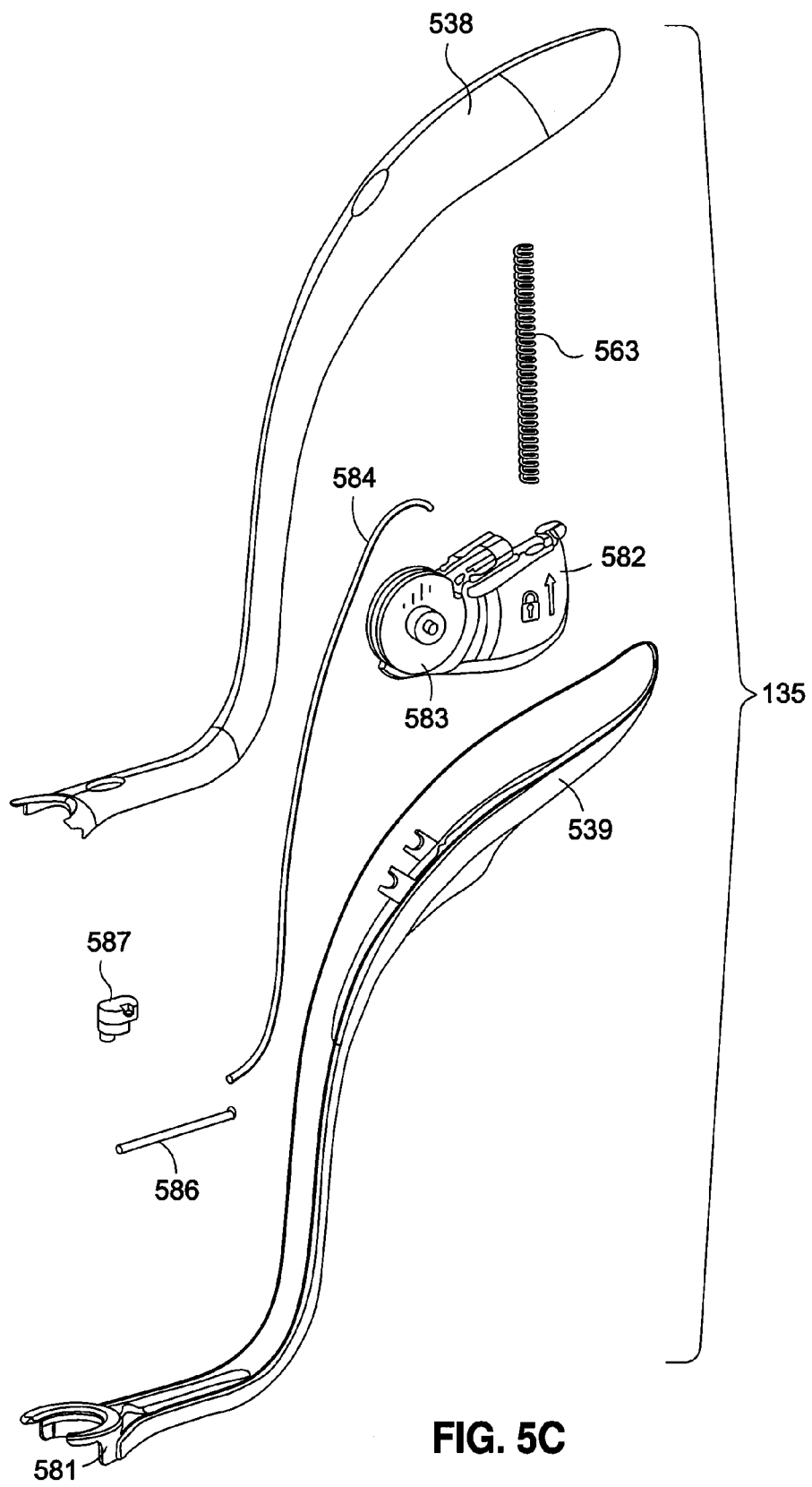
FIG. 5C illustrates an exploded, perspective view of an applier tool according to an embodiment of the present invention.

In accordance with various embodiments, FIGS. 5A-5C illustrate an applier 135 that is configured to interface with the top portion 205 of the port 130. The applier 135 includes an applier housing 539 and a housing top cover 538. The applier 135 further includes a head or a gripping portion 581 configured to mate with the top portion 205 of the port 130.

A trigger 582 is movably coupled to the applier housing 539 to allow a physician to actuate the port 130 in order to implant the anchors 255. The trigger 582 is biased away from the applier housing 539 via a spring 563. The trigger 582 is also coupled to a pulley 583. The pulley 583 is coupled to a first drive band 584, and the first drive band 584 is coupled to a second drive band 586 to facilitate actuating the port 130, as will be described further below. The first and second drive bands 584, 586 may be made of NITL, and other components of the applier 135 may be made of plastic and/or may be designed to be disposable. A switch 587 is operatively coupled to the applier housing 539 to direct the second drive band 586 in an implanting direction or a removal direction to facilitate implanting or removing the port 130, which will also be discussed further below.

Figure 6A:
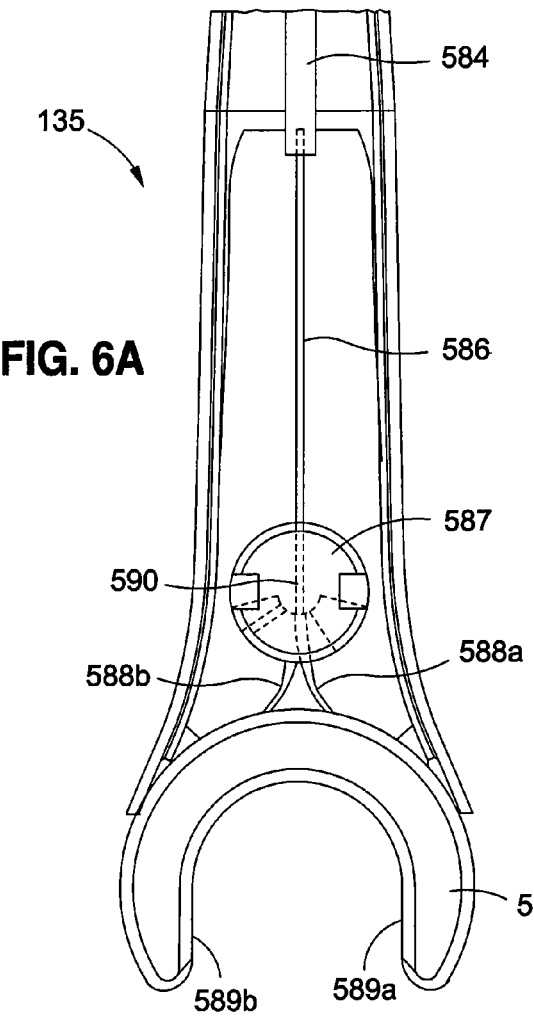
FIG. 6A illustrates a sectional view of a gripping end of an applier tool according to an embodiment of the present invention.
Figure 6B:
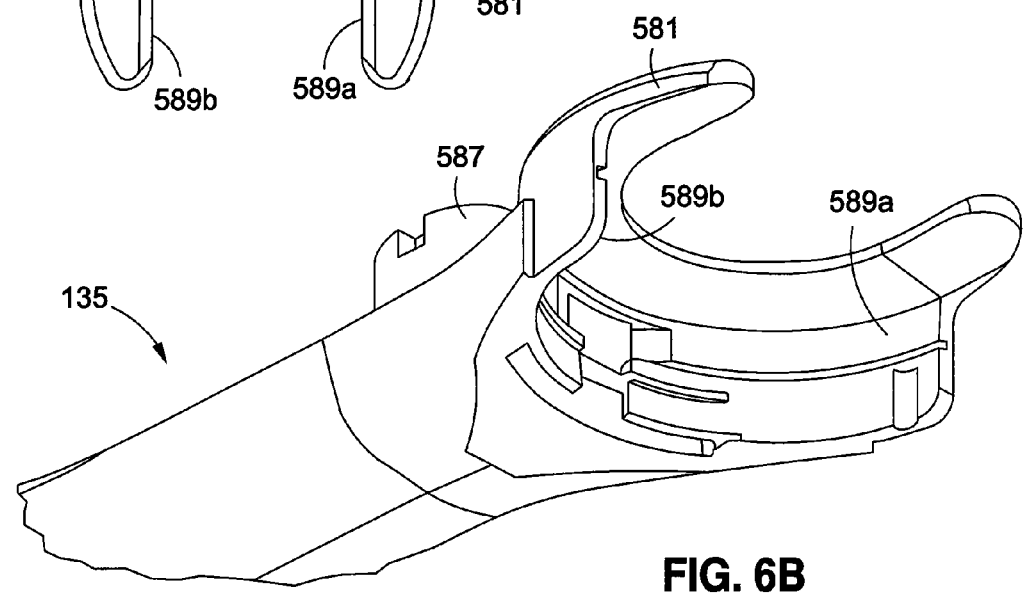
FIG. 6B illustrates a perspective view of a gripping end of an applier tool according to an embodiment of the present invention.

In accordance with an embodiment of the present invention, and with reference to FIGS. 6A-6B, the first drive band 584 may be referred to as a horizontal drive band. To clarify, and with reference specifically to FIG. 6A, in an embodiment, the first drive band 584 may be a substantially flat drive band with a horizontal orientation, with respect to the gripping portion 581 of the applier 135, where the first drive band 584 mates with the second drive band 586.

Further, in an embodiment, the second drive band 586 may be referred to as a vertical drive band because of the second drive band's 586 vertical orientation, with respect to the gripping portion 581, where the first drive band 584 mates with the second drive band 586. Such a configuration allows the first drive band 584 to curve up the applier housing 539, and allows the second drive band 586 to curve with respect to the curvature of the gripping portion 581 of the applier 135. Other orientations and geometries of the drive bands 584, 586 that facilitate rotating the top portion 205 of the port 130 in response to a depression of the trigger 582 are contemplated within the scope of the present invention.

The switch 587 may further comprise a switch channel 590 configured to receive the second drive band 586 and direct the second drive band 586 through a first band channel 588a or a second band channel 588b in the applier 135. The switch 587 may rotate automatically or manually to direct the second drive band 586 down the appropriate band channel 588a, 588b. For example, a physician may rotate the switch 587 depending on whether or not the port 130 will be implanted or removed. In another embodiment, the switch 587 may automatically toggle to a removal position after the trigger 582 is depressed and released to implant the port 130.

Figure 8A:
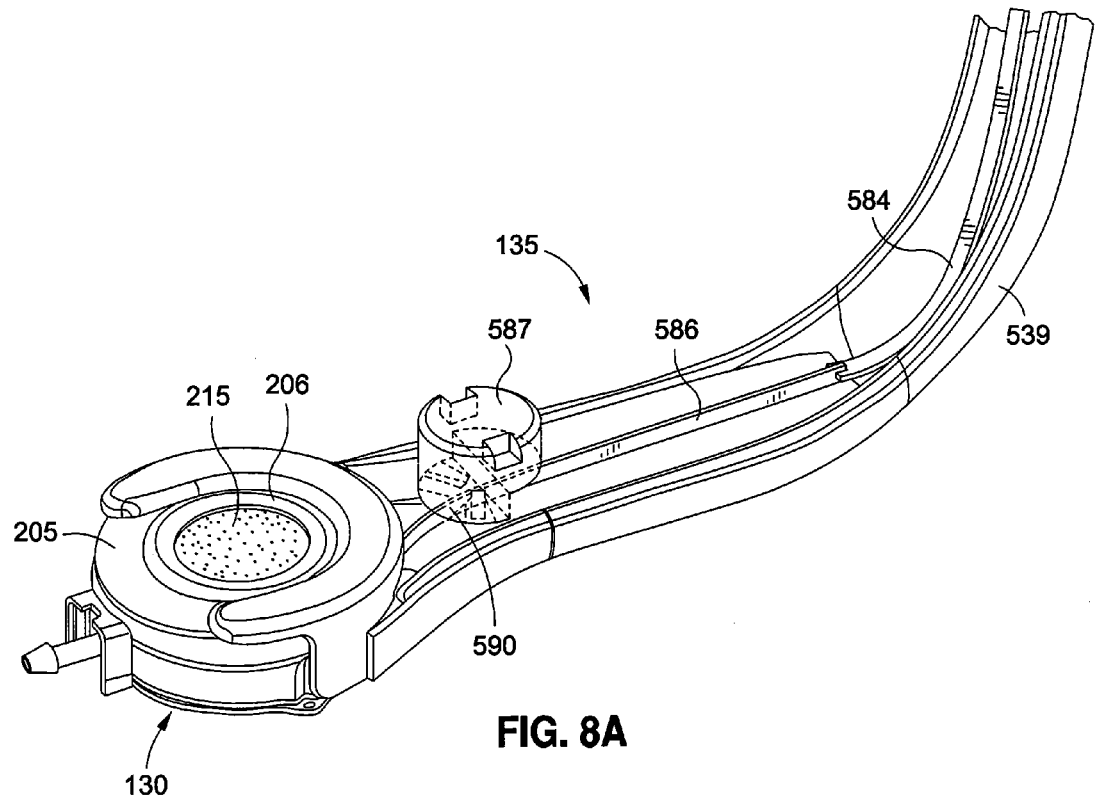
FIG. 8A illustrates a perspective view of an applier tool without a housing cover, where the applier tool is mated with an implantable injection port according to an embodiment of the present invention.
Figure 8B:
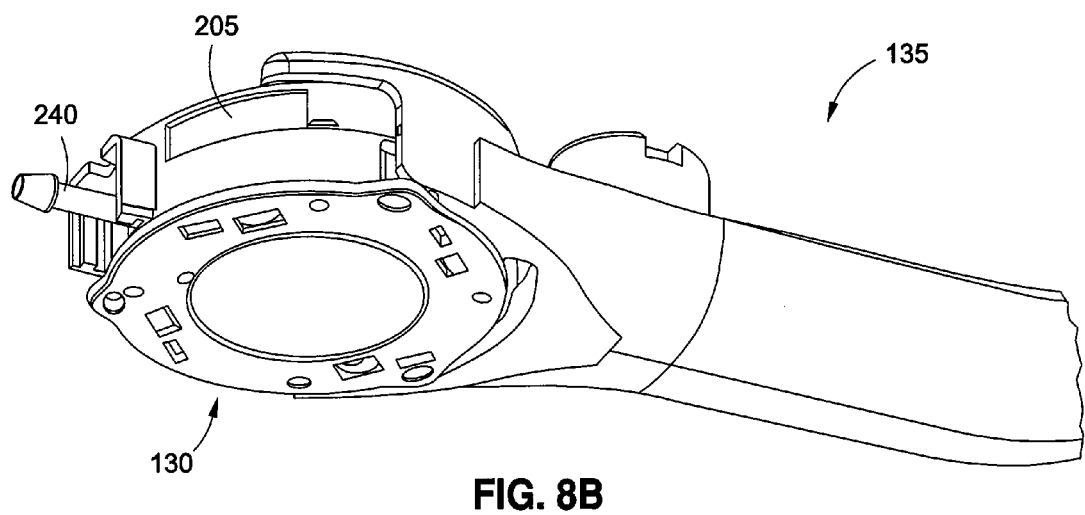
FIG. 8B illustrates a perspective view of an applier tool mated with an implantable injection port according to an embodiment of the present invention.

For example, to implant the port 130, the switch channel 590 may direct the second drive band 586 through the first band channel 588a so that the second drive band 586 moves clockwise along a first band surface 589a of the gripping portion 581. FIGS. 6C-6D illustrate the extended second drive band 586 along the first band surface 589a to illustrate the motion along the first band surface 589a (without showing the connected port 130) according to an embodiment of the present invention. With momentary reference to FIGS. 8A-8B, in accordance with an embodiment, a partial perspective view of the applier 135 gripping the port 130 is shown, with the second drive band 586 passing through the switch, but prior to beginning rotation of the top portion 205 to implant the port 130.

In this manner, the second drive band 586 may be configured to interface with the top portion 205 of the port 130 to rotate the top portion 205 in a clockwise fashion in order to implant the anchors 255 in the tissue of the patient 105. For example, with reference also to FIGS. 2A, 11, and 13-14, the second drive band 586 may be configured to interface with a lip 261 on the top portion 205 to facilitate rotating the top portion 205 clockwise by pushing against the lip 261.

The lip 261 may be referred to as an implanting lip because the second drive band 586 pushes against the implanting lip 261 to implant the port 130. A similar lip 262 (see FIG. 2A) may be located on another part of the top portion 205 to allow the second drive band 586 to push against the lip 262 to rotate the top portion 205 counter-clockwise. The lip 262 may be referred to as a removal lip because the second drive band 586 pushes against the removal lip 262 to remove the port 130.

Accordingly, the first band channel 588a may be referred to as an implanting band channel, the first band surface 589a may be referred to as an implanting band surface, and the second drive band 586 may cause the top portion 205 to move in an implanting direction by pushing against the lip 261 when the second drive band 586 moves through the implanting band channel 588a and along the implanting band surface 589a.

Similarly, to remove the port 130, the switch channel 590 may direct the second drive band 586 through the second band channel 588b so that the second drive band 586 moves counter-clockwise along a second band surface 589b of the gripping portion 581. FIGS. 6E-6F illustrate the extended second drive band 586 along the second band surface 589b to illustrate the motion along the second band surface 589b (without showing the connected port 130) according to an embodiment of the present invention.

In this manner, the second drive band 586 may be configured to interface with the top portion 205 of the port 130 to rotate the top portion 205 in a counter-clockwise fashion in order to remove the anchors 255 from the tissue of the patient 105. For example, the second drive band 586 may interface with a lip 262 (see FIG. 2A), ridge, or other structure on the top portion 205 to facilitate pushing on the structure to rotate the top portion 205 in a counter-clockwise direction. The lip 262 may be referred to as a removal or an extraction lip because the second drive band 586 pushes against the removal lip 262 to remove the port 130.

Accordingly, the second band channel 588b may be referred to as a removal band channel, the second band surface 589b may be referred to as a removal band surface, and the second drive band 586 may cause the top portion 205 to move in a removal direction when the second drive band 586 moves through the removal band channel 588a and along the removal band surface 589a. However, in other embodiments, it should be understood that the top portion 205 of the port 130 may be rotated counter-clockwise to implant the anchors 255 and rotated clockwise to remove the anchors 255. In various embodiments, the applier 135 may provide a tactile response, for example, through the trigger 582, to indicate implantation and/or removal of the anchors 255.

In various embodiments, the applier tool 135 may be assembled as follows. The vertical drive band 586 and the horizontal drive band 584 may be assembled together using a snap fit or an assembly pin, or other suitable attachment mechanism. The horizontal drive band 584 may then be inserted into the trigger 582, for example, into a groove in the pulley 583. A snap fit, assembly pin, or other suitable mechanism may be used to attach the horizontal drive band 584 to the trigger 582. The spring 563 is then inserted into the trigger 582, and the assembly is inserted into the applier housing 539. The switch 587 is then inserted into the housing 539, and the housing top cover 538 is then secured to the housing 539, for example, by bonding the top cover 538 and the housing 539 together using epoxy or ultrasonic welding.

Figure 7A:
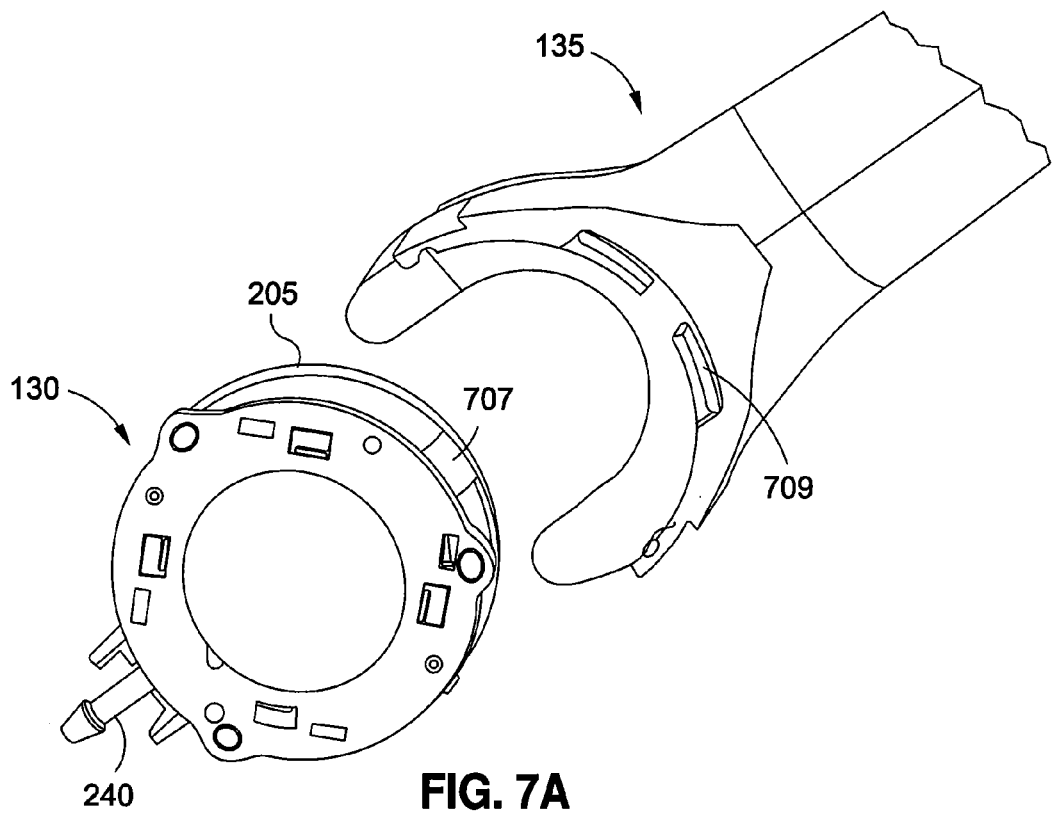
FIG. 7A illustrates a bottom view of an applier tool separated from an implantable injection port according to an embodiment of the present invention.
Figure 7B:
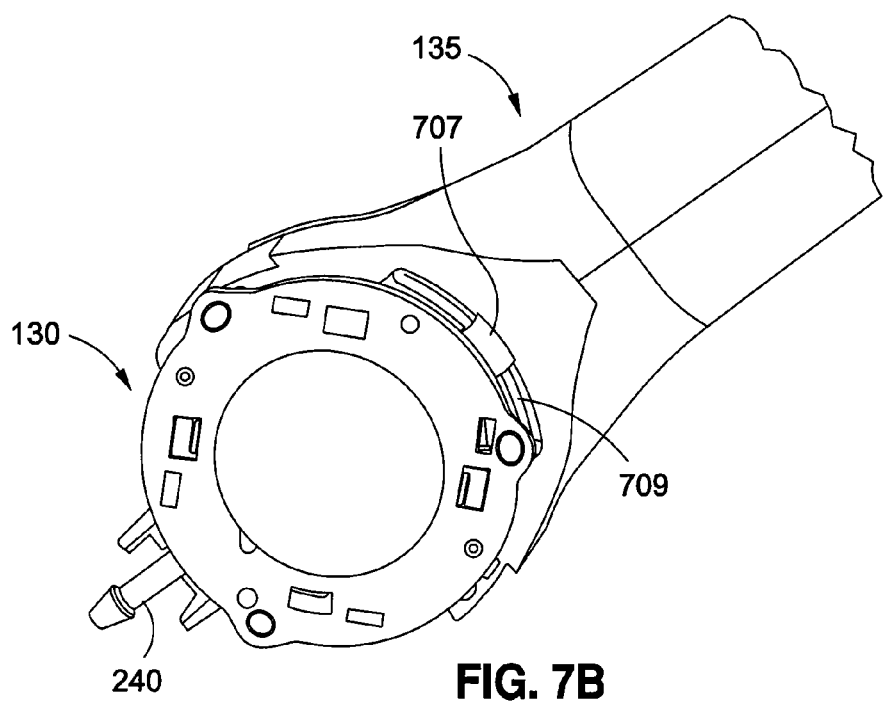
FIG. 7B illustrates a bottom view of an applier tool mated with an implantable injection port according to an embodiment of the present invention.

With reference to FIGS. 7A-7B, in accordance with an embodiment, the top portion 205 may comprise one or more fittings 707 (e.g., cavities, holes, snap bosses, or notches) located on a surface of the top portion 205 to allow the applier 135 to attach to or mate with the top portion 205. The fittings 707 may be referred to as snap fittings or bosses because the applier 135 may snap into and out of the fittings 707. The fittings 707 may interface with mating snap leaves 709 on the applier 135. In one embodiment, the top portion 205 rotates in a clockwise or counter-clockwise direction as guided by the applier 135 to facilitate implanting the port 130 into or removing the port 130 from the patient's tissue. The port 130 may be released from the applier 135 by slightly lifting and then retracting the applier 135.

Figure 9:
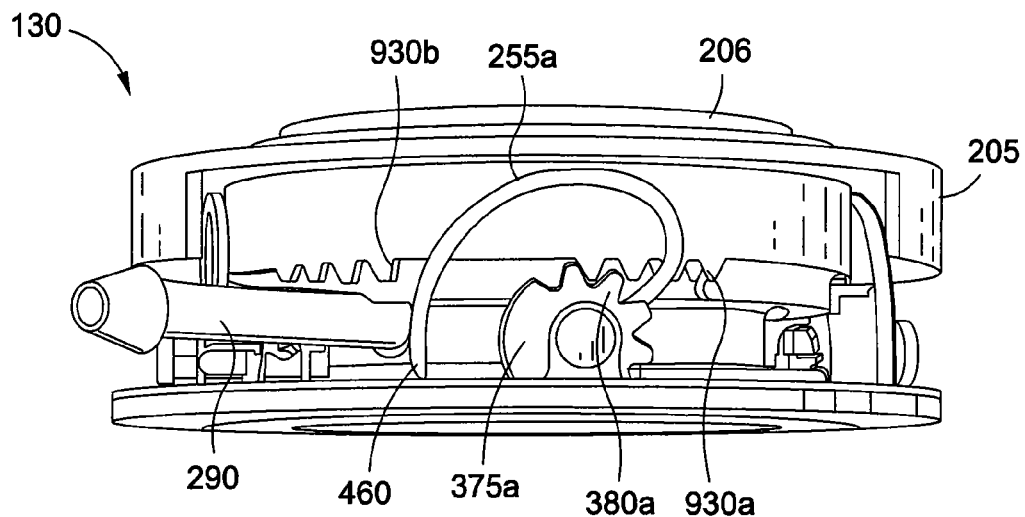
FIG. 9 illustrates an anchor in an undeployed position in an implantable injection port according to an embodiment of the present invention.

With reference to FIG. 9, in an embodiment, the top portion 205 of the port 130 may have top teeth 930 protruding from a bottom surface of the top portion 205. In an example embodiment, the top teeth 930 are positioned about an axis that is substantially perpendicular to a plane defined by the top portion 205. The top teeth 930 include ridges, alternating cut-outs and protrusions, bumpy or uneven surfaces, a flat surface with friction and/or any other surface(s) with sufficient friction to interact with and move components (e.g., the gear 375 and the anchor 255) of the port 130. Various sets or pluralities of top teeth 930 (e.g., a first set/plurality of top teeth, a second set/plurality of top teeth, etc.) may be positioned along an outer edge of the top portion 205 for interacting with different gears 375 at different or the same times.

The gear 375 may also be referred to as a pinion gear. The teeth 380 on the gear 375 mate with the top teeth 930 of the top portion 205 to rotate the anchor 255. The teeth 380 and top teeth 930 may include ridges, bumpy surfaces, flat surfaces with friction, and any other surface with sufficient friction to interact with and to move components of the port 130.

Figure 10:
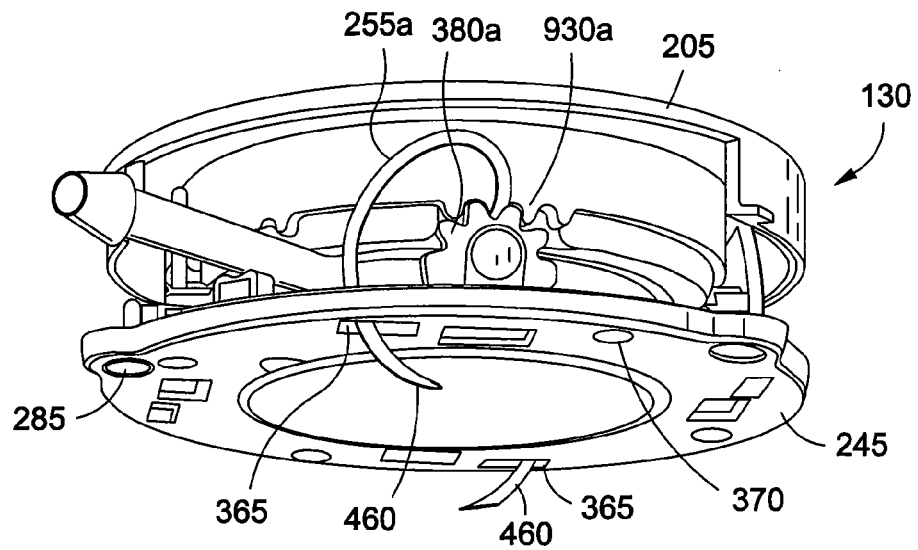
FIG. 10 illustrates two anchors in a partially deployed position in an implantable injection port according to an embodiment of the present invention.

With reference to FIG. 10, and in accordance with an embodiment, to deploy the anchor 255, the top portion 205 is rotated in a clockwise direction and the top teeth 930 are engaged with the teeth 380 to rotate the gear 375 and the anchor 255 in a counter-clockwise direction causing the anchor 255 to move through the anchor opening 365 and into the tissue of a patient. In an embodiment, and with reference to FIG. 11, the anchor tip 460 may also move into the tip opening 370 when the anchor 255 is fully deployed.

The anchor 255 secures the port 130 to the human 105, by the anchor tip 460 penetrating the human's skin or muscle (e.g., abdominal muscle fascia). The anchor tip 460 may also be referred to as a hook or pointed end. The anchor tip 460 is structured to penetrate and enter the bodily tissue as the anchor 255 rotates into the deployed position.

In some embodiments, the anchor tip 460 includes one or more flat faces. For example, the anchor tip 460 may have a single facet, or may have two or more facets. The anchor 255 may also be referred to as an attachment mechanism, a hook, a needle anchor, a needle device, or a cork screw. Also, the anchor 255 may be formed in the shape of a hook, a needle or a cork screw (e.g., a series of spirals with a sharp point at the end of the series of spirals). In one embodiment, each anchor 255 may be made of a wire, for example, a bent stainless steel wire having a round cross section and a multi-faceted sharp distal tip. The port 130 may include two, three, four, five or more anchors 255 and related components that are attached and positioned equidistantly around the base 245.

In one embodiment, a plurality of anchors 255 are deployed or moved from an un-deployed position (see, e.g., FIG. 9) to a fully-deployed position (see, e.g., FIGS. 13B, 13C, and 14), or from a fully-deployed position to an un-deployed position. In various embodiments, some anchors 255 may be deployed or removed simultaneously. For example, where the port 130 has four anchors 255, and with reference to FIGS. 10 and 11A-11B, opposite anchors 255 may be simultaneously deployed. Further, some anchors 255 may be deployed or removed non-simultaneously. For example, a first set of opposing anchors 255a may be deployed or removed first, and then a second set of opposing anchors 255b may be deployed or removed second (see, e.g., FIG. 13A). It should be understood that various other deployment combinations, both simultaneous and non-simultaneous, are contemplated within the scope of the present invention.

Each anchor 255 is rotated from an un-deployed position where the anchor 255 is above the base 245 to a deployed position where the anchor 255 travels through the anchor opening 365. When in the deployed position, the anchors 255 fix the port 130 to the bodily tissue. If the port 130 is removed, the anchors 255 may be rotated from the deployed position back to the un-deployed position within the port 130.

In the case where the port 130 is used in conjunction with the gastric band 110, the port 130 may be secured, by means of the anchors 255, to the rectus muscle fascia. The anchor 255 may protrude through the anchor opening 365 in the base 245, and may also protrude through the tip opening 370 in the base 245 as the anchor 255 is rotated around the axle 350. The tip opening 370 provides a safe storage position for the anchor tip 460 so the anchor tip 460 does not get dulled or damaged.

The base 245 may also have one or more suture holes 285 for suturing the port 130 to the human 105, in the event that the use of the applier 135 to attach the port 130 is not desired or allowable. A drawback of suturing is the additional time and effort required by the medical professional to secure the port 130 during surgery.

In some embodiments, the anchors 255 are removable or reversible, allowing the anchors 255 to be detached from the bodily tissue. For example, the top portion 205 can be rotated in a counter-clockwise direction to remove the anchors 255 from the tissue. Specifically, to un-deploy the anchors 255, the top portion 205 is rotated in a counter-clockwise direction and the top teeth 930 are engaged with the teeth 380 to rotate the gear 375 and the anchor 255 in a clockwise direction causing the anchors 255 to move through the anchor opening 365 and out of the tissue. The anchor tip 460 may also move into the anchor opening 365.

In one embodiment, a plurality of anchors 255 includes four anchors that are evenly spaced apart around the base 245. Each anchor 255 may be referred to as being independent, which includes being a separate component or having separate operation from another anchor 255. Each anchor 255 includes a curved distal portion such as the anchor tip 460 which engages the bodily tissue and a pivotal proximal portion or a body portion that includes the gear 375, which is rotatably connected to the base 245 of the port 130.

As noted above, in various embodiments, the anchors 255 are independently movable between a non-implanted and implanted position. Furthermore, the anchors 255 may be implanted or extracted simultaneously or non-simultaneously. To facilitate deployment of the anchors 255, the plurality of sets of top teeth 930 may be advantageously located around a circumference of the top portion 205 so that the top teeth 930 interact with the teeth 380 at the appropriate time.

Although it should be understood that various numbers, configurations, and locations of the top teeth 930, the gears 375, and the anchors 255 are contemplated within the scope of the present invention, the following is a description of a particular configuration according to an embodiment of the present invention.

With reference to FIGS. 9, 10, and 11A-B, and in accordance with an embodiment, the top portion 205 includes four sets of top teeth 930. Each set of top teeth 930 is located to allow simultaneous or non-simultaneous deployment of the anchors 255. For example, the four anchors 255 may be spaced equidistantly around the circumference of the port 130 (e.g., every ninety degrees), but the sets of top teeth 930 may not be equidistant.

Figure 11A:
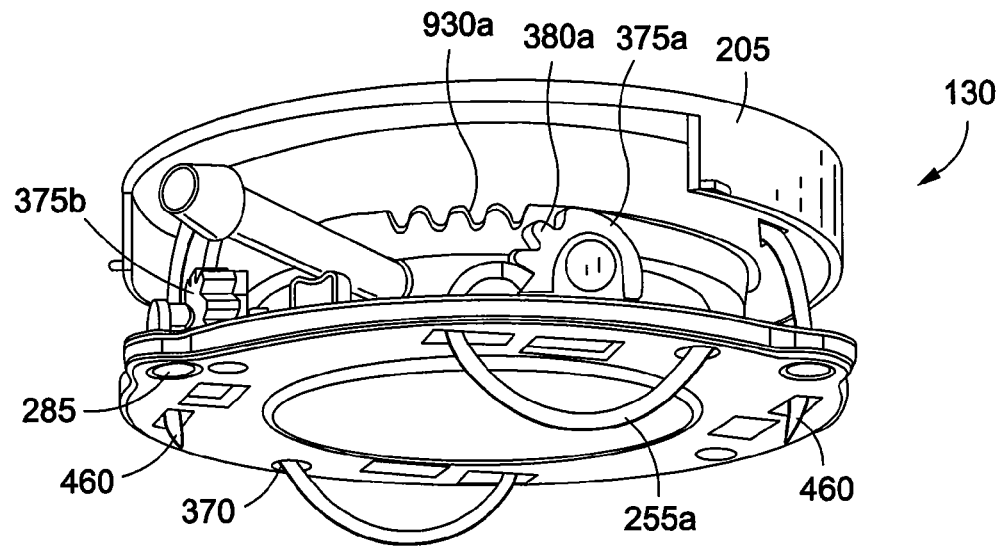
FIG. 11A illustrates two anchors in a deployed position according to an embodiment of the present invention.
Figure 11B:
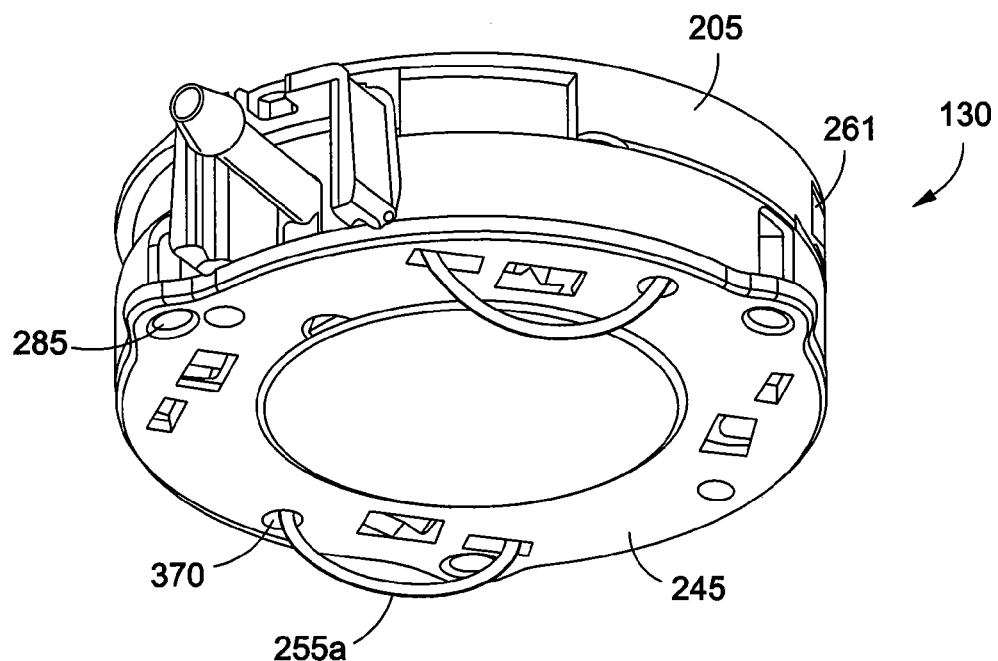
FIG. 11B illustrates another view of two anchors in a deployed position according to an embodiment of the present invention.
Figure 12:
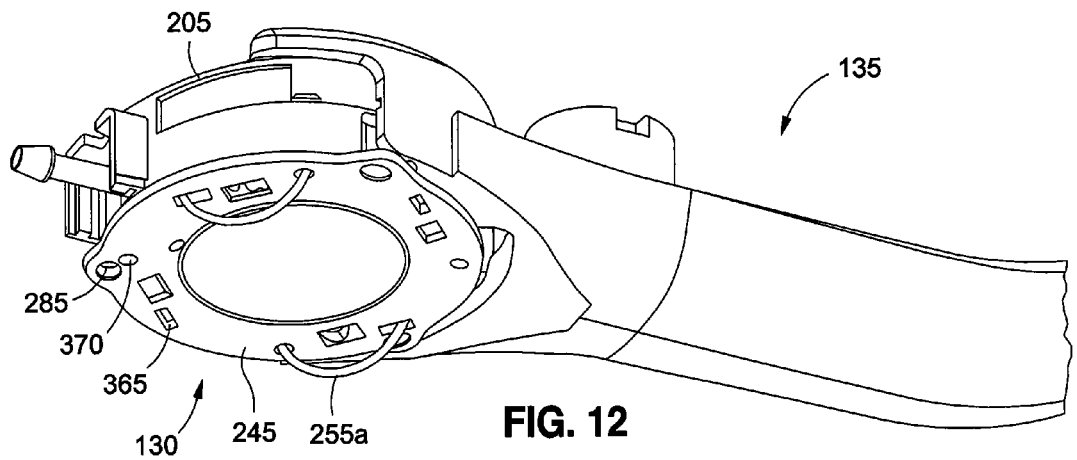
FIG. 12 illustrates a perspective view of an applier tool mated with an implantable injection port having two deployed anchors according to an embodiment of the present invention.
Figure 13A:
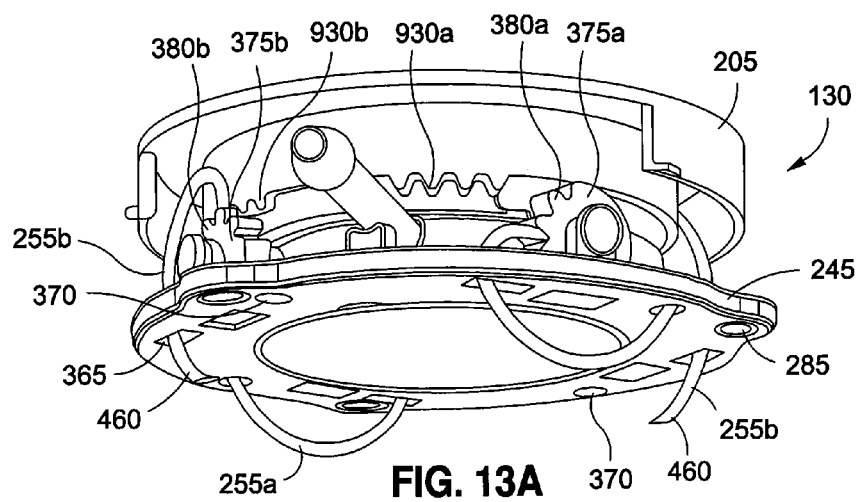
FIG. 13A illustrates an implantable injection port with two deployed anchors and two partially deployed anchors according to an embodiment of the present invention.
Figure 13B:
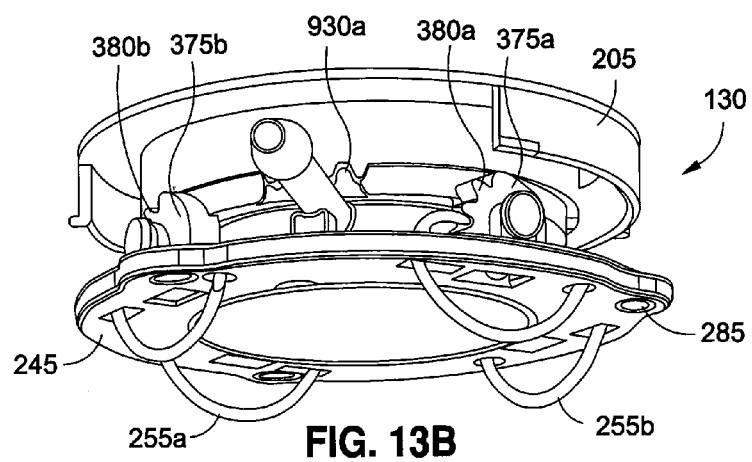
FIG. 13B illustrates an implantable injection port with four deployed anchors according to an embodiment of the present invention.
Figure 13C:
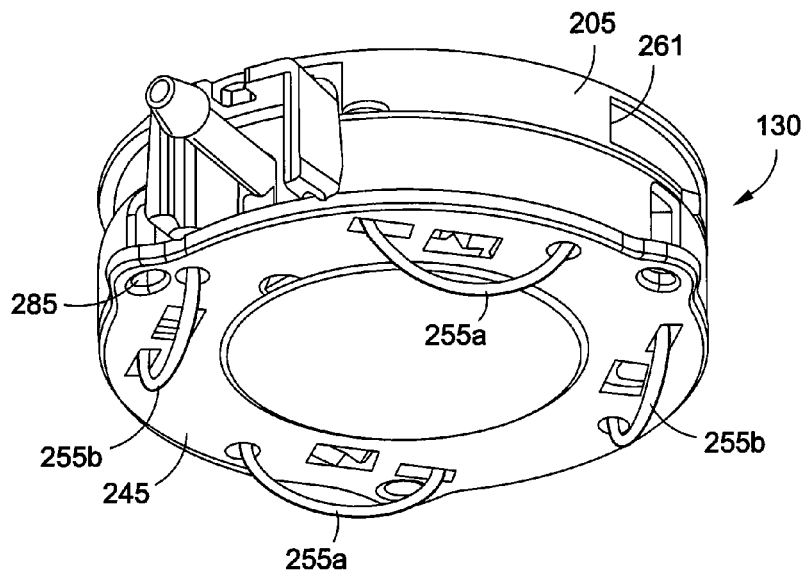
FIG. 13C illustrates a perspective view of an implantable injection port with four deployed anchors according to an embodiment of the present invention.
Figure 14:
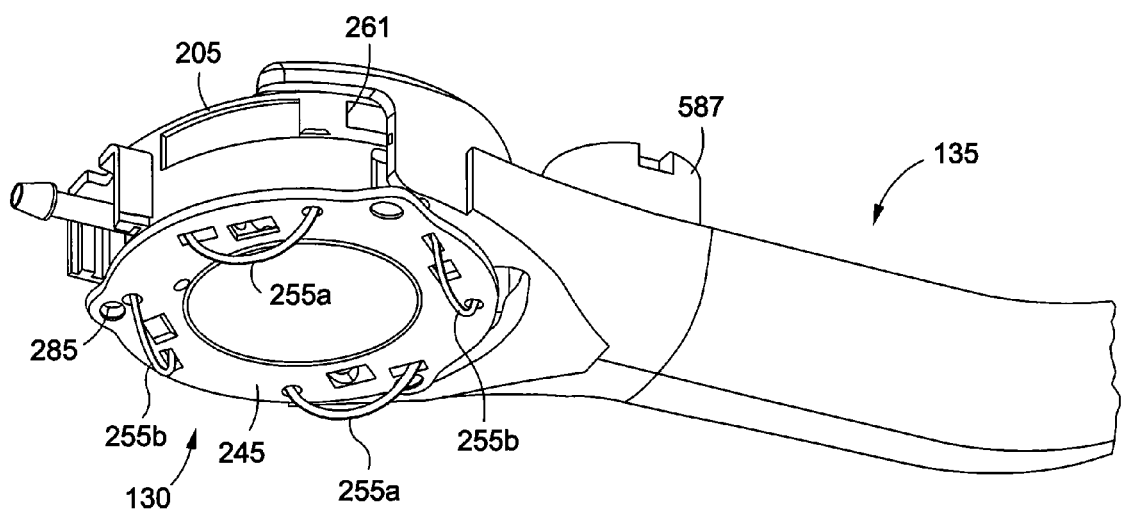
FIG. 14 illustrates a perspective view of an applier tool mated with an implantable injection port having four deployed anchors according to an embodiment of the present invention.

To explain, a first set of the anchors 255a that are opposite each other may be deployed first, and a second set of anchors 255b (see FIGS. 13A-13C) that are opposite each other, but that neighbor the first set of anchors 255a, may be deployed second. A first set of top teeth 930a (as illustrated in FIG. 9) may interface with the teeth 380a on a first gear 375a (or first set of gears 375a) to facilitate implanting a first anchor 255a (or first set of anchors 255a) into the patient's tissue. As illustrated in FIGS. 10 and 11A-11B, these first anchors 255a are implanted prior to implantation of a second set of anchors 255b (see FIG. 13B-13C).

In an embodiment, and with reference to FIGS. 13A-13C and 14, after the first set of top teeth 930a moves through the teeth 380a on the first set of gears 375a and the first set of anchors 255a are implanted, the second set of top teeth 930b interact with the second set of teeth 380b on the second set of gears 375b. In this manner, the second set of top teeth 930b cause the second set of anchors 255b to be implanted into the tissue of the patient after implantation of the first set of anchors 255a. The anchors 255 may similarly be non-simultaneously removed from the patient's tissue in reverse of the above mentioned process (e.g., by rotating the top portion 205 counter-clockwise).

Although two sets of top teeth 930a, 930b have been disclosed, it should be understood that only one set of top teeth 930 may be included in accordance with an embodiment. For example, the set of top teeth 930 may include discrete portions of top teeth 930 that are located opposite from each other along the circumference of the top portion 205. In this manner, the top teeth 930 may first come in contact with the first set of teeth 380a on the first set of gears 375a to facilitate implanting the first set of anchors 255a. As the top portion 205 continues to rotate, the top teeth 930 may then come into contact with the second set of teeth 380b on the second set of gears 375b to facilitate implanting the second set of anchors 255b. Other configurations are contemplated within the scope of the present invention that facilitate non-simultaneous deployment of at least some of the anchors 255.

In accordance with various embodiments, non-simultaneous implantation of the anchors 255 may be accomplished by moving the switch 587 of the applier 135 to an implantation position and then depressing the trigger 582 of the applier 135. Depressing the trigger 582 causes the horizontal drive band 584 to act on the vertical drive band 586, which moves through the switch channel 590 and the implanting band channel 588a.

By moving through the implanting band channel 588a, the vertical drive band 586 acts on the implanting lip 261 to cause the top portion 205 to rotate in a clockwise manner to move the top teeth 930 over the teeth 380 of the gears 375 to implant the anchors 255 into the tissue of the patient. For example, the first set of anchors 255a may be deployed, and then the second set of anchors 255b may be deployed, resulting in non-simultaneous deployment of the anchors 255a, 255b.

In a reverse manner, and in accordance with various embodiments, non-simultaneous removal of the anchors 255 may be accomplished by moving the switch 587 of the applier 135 to a removal position and then depressing the trigger 582 of the applier 135. Depressing the trigger 582 causes the horizontal drive band 584 to act on the vertical drive band 586, which moves through the switch channel 590 and the removal band channel 588b.

By moving through the removal band channel 588b, the vertical drive band 586 acts on the removal lip 262 to cause the top portion 205 to rotate in a counter-clockwise manner to move the top teeth 930 over the teeth 380 of the gears 375 to remove the anchors 255 from the tissue of the patient. For example, the first set of anchors 255a may be removed, and then the second set of anchors 255b may be removed, resulting in non-simultaneous removal of the anchors 255a, 255b.

The terms "a," "an," "the," and similar referents used in the context of describing the present invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the present invention otherwise claimed. No language in the specification should be construed as indicating any non-claimed element essential to the practice of the present invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described herein.

The previous description of the disclosed examples is provided to enable any person of ordinary skill in the art to make or use the disclosed methods and apparatus. Various modifications to these examples will be readily apparent to those skilled in the art, and the principles defined herein may be applied to other examples without departing from the spirit or scope of the disclosed method and apparatus. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. An implantable injection port for use with a gastric band for treating obesity and for attaching to a tissue of a patient, the implantable injection port comprising:
    a base having a first anchor opening;
    a first gear coupled to the base and rotatable about a first axis, the first gear having a first plurality of gear teeth;
    a second gear coupled to the base and rotatable about a second axis, the second gear having a second plurality of gear teeth;
    a first anchor coupled to the first gear;
    a second anchor coupled to the second gear; and
    a top portion spaced apart from the base and having a first plurality of top teeth that engage with the first plurality of gear teeth on the first gear prior to rotation of the second gear, the top portion being rotatable causing rotation of the first gear such that the rotation of the first gear causes movement of the first anchor through the anchor opening of the base and into the tissue of the patient,
    wherein subsequent to the first plurality of top teeth rotating a predetermined amount with the first plurality of gear teeth on the first gear, the first plurality of top teeth are configured to begin to rotate with the second plurality of gear teeth on the second gear and cause rotation of the second gear to begin subsequent to a beginning rotation of the first gear, which causes movement of the second anchor through a second anchor opening of the base and into the tissue of the patient.

2. The implantable injection port of claim 1, wherein the first gear rotates about the first axis independently of the second gear.

3. The implantable injection port of claim 1, wherein the first anchor and the second anchor move non-simultaneously into the tissue of the patient.

4. The implantable injection port of claim 1, wherein the first anchor moves into the tissue of the patient at a first time, and wherein the second anchor moves into the tissue of the patient a second time different than the first time.

5. The implantable injection port of claim 1, further comprising a third gear coupled to the base and rotatable about a third axis, the third gear having a third anchor and a third plurality of gear teeth.

6. The implantable injection port of claim 5, wherein the top portion comprises a second plurality of top teeth that engage with the third plurality of gear teeth on the third gear to cause movement of the third anchor through a third anchor opening of the base and into the tissue of the patient.

7. The implantable injection port of claim 6, wherein the second plurality of top teeth engage with the third plurality of gear teeth simultaneously with the engagement of the first plurality of top teeth and the first plurality of gear teeth.

8. The implantable injection port of claim 6, wherein the second plurality of top teeth engage with the third plurality of gear teeth at a first time, and wherein the first plurality of top teeth engage with the first plurality of gear teeth at the first time.

9. The implantable injection port of claim 5, wherein the third axis is collinear with the first axis.

10. The implantable injection port of claim 1, wherein the implantable injection port is constructed to be actuated with an actuation device capable of non-simultaneously rotating the first gear and the second gear to attach the implantable injection port to the tissue of the patient with.

11. The implantable injection port of claim 1, further comprising a septum positioned within a center opening of the top portion and made of a self sealing needle penetrable material.

12. The implantable injection port of claim 11, further comprising a reservoir positioned underneath the septum and between the top portion and the base for holding fluid.

13. The implantable injection port of claim 1, wherein the first and second gears are constructed to rotate with the rotation of the first plurality of top teeth with the first plurality of gear teeth and the second plurality of gear teeth causes the first anchor to be fully deployed before the second anchor is fully deployed.

14. An actuation device for attaching an implantable injection port to a tissue of a patient, the actuation device comprising:
a head configured to be coupled to the implantable injection port;
a first drive band coupled to a trigger of the actuation device;
a second drive band coupled to the first drive band for translating motion from the trigger of the actuation device to the second drive band, wherein the second drive band is configured to interface with a top portion of the implantable injection port to facilitate deploying an anchor of the implantable injection port into the tissue of the patient; and
a switch operable to direct the second drive band along a first surface of the head to rotate the top portion of the implantable injection port in an implanting direction and to direct the second drive band along a second surface of the head to rotate the top portion of the implantable injection port in a retracting direction.

15. The actuation device of claim 14, wherein a face of the first drive band is substantially perpendicular to a face of the second drive band, and wherein the first drive band is a horizontal drive band and the second drive band is a vertical drive band.

16. The actuation device of claim 14, wherein the head is a gripping portion configured to be coupled to the implantable injection port via a snap feature.

17. The actuation device of claim 14, wherein the implanting direction of the top portion facilitates implanting the anchor in the tissue of the patient, and wherein the retracting direction of the top portion facilitates retracting the anchor from the tissue of the patient.

18. The actuation device of claim 14, wherein the implanting direction is clockwise and the retracting direction is counter clockwise.

19. The actuation device of claim 14, wherein the switch is manually or automatically toggled to a retracting mode after the trigger is depressed and released to implant the anchor in the tissue of the patient.

20. The actuation device of claim 19, wherein the switch is toggled by rotating from a first position to a second position, wherein the first position guides the second drive band to rotate the top portion of the implantable injection port in the implanting direction, and wherein the second position guides the second drive band to rotate the top portion of the implantable injection port in the retracting direction.

21. A method for implanting an implantable injection port in a tissue of a patient, the method comprising:
coupling a gripping portion of an actuation device to a top portion of the implantable injection port having a rotatable top portion having a first set of top teeth configured to alternately rotate with a first gear and a second gear, the first gear coupled to a first anchor and the second gear coupled to a second anchor;
depressing a trigger of the actuation device having a switch configured in an implanting orientation;
responsive to depressing the trigger, directing a vertical drive band through the switch to push the top portion of the implantable injection port to rotate the top portion in an implanting direction;
rotating the rotatable top portion; and
implanting, at a first time during the rotation of the top portion, a first anchor into the tissue of the patient in response to the first set of top teeth rotating a first predetermined amount with the first gear and implanting, at a second time during the rotation of the top portion subsequent to the first set of top teeth rotating the first predetermined amount with the first gear, the second anchor into the tissue of the patient in response to the first set of top teeth rotating with the second gear subsequent to the first set of top teeth rotating the first predetermined amount with the first gear.

22. The method according to claim 21, further comprising toggling the switch to an extracting orientation in response to the trigger being released.

23. A system for implanting an implantable injection port in a tissue of a patient, the system comprising:
an actuation device for attaching the implantable injection port to the tissue of the patient, the actuation device comprising:
a head configured to be coupled to the implantable injection port;
a first drive band coupled to a trigger of the actuation device;
a second drive band coupled to the first drive band for translating motion from the trigger of the actuation device to the second drive band, wherein the second drive band is configured to interface with a top portion of the implantable injection port to facilitate deploying an anchor of the implantable injection port into the tissue of the patient; and
a switch operable to direct the second drive band to rotate the top portion of the implantable injection port in an implanting direction or a retracting direction;
wherein the implantable injection port comprises:
a base having an anchor opening;
a first gear coupled to the base and rotatable about a first axis, the first gear having a first plurality of gear teeth; and
a second gear coupled to the base and rotatable about a second axis, the second gear having a second plurality of gear teeth;
wherein the anchor is coupled to the first gear, and
wherein the top portion is spaced apart from the base and has a first plurality of top teeth that engage with the first plurality of gear teeth on the first gear prior to a second plurality of top teeth engaging with the second plurality of gear teeth on the second gear, the top portion being rotatable causing rotation of the first gear such that the rotation of the first gear causes movement of the anchor through the anchor opening of the base and into the tissue of the patient.

24. An implantable injection port for use with a gastric band for treating obesity and for attaching to a tissue of a patient, the implantable injection port comprising:
a base having a first anchor opening;
a first gear coupled to the base and rotatable about a first axis, the first gear having a first plurality of gear teeth;
a second gear coupled to the base and rotatable about a second axis, the second gear having a second plurality of gear teeth;

a first anchor coupled to the first gear;
a second anchor coupled to the second gear; and
a top portion spaced apart from the base and having a first plurality of top teeth and a second plurality of top teeth angularly spaced from the first plurality of top teeth, the first plurality of top teeth engagable with the first plurality of gear teeth on the first gear and the second plurality of top teeth engageable with the second plurality of gear teeth on the second gear when the first plurality of top teeth are disengaged from the first plurality of gear teeth, the top portion being rotatable to cause rotation of the first gear and the first anchor at a first time and to cause rotation of the second gear and the second anchor at a second time subsequent to the first time.

25. An implantable injection port for use with a gastric band for treating obesity and for attaching to a tissue of a patient, the implantable injection port comprising:
   a base having a first anchor opening and a second anchor opening;
   a first gear coupled to the base and rotatable about a first axis, the first gear having a first plurality of gear teeth;
   a second gear coupled to the base and rotatable about a second axis, the second gear having a second plurality of gear teeth;
   a first anchor coupled to the first gear;
   a second anchor coupled to the second gear; and
   a top portion spaced apart from the base and having a first plurality of top teeth and a second plurality of top teeth circumferentially spaced from the first plurality of top teeth, the first plurality of top teeth configured to engage with the first plurality of gear teeth on the first gear prior to the second plurality of top teeth engaging with the second plurality of gear teeth on the second gear when the top portion is rotated, the top portion being configured to rotate and cause rotation of the first gear and the second gear such that the rotation of the first gear causes movement of the first anchor through the first anchor opening of the base and into the tissue of the patient and rotation of the second gear causes movement of the second anchor through the second anchor opening and into the tissue of the patient,
   wherein subsequent to the first plurality of top teeth rotating a predetermined amount with the first plurality of gear teeth on the first gear, the second plurality of top teeth begins to rotate with the second plurality of gear teeth on the second gear to cause rotation of the second gear to begin subsequent to beginning rotation of the first gear, which causes movement of the second anchor through the second anchor opening of the base.

26. The implantable injection port of claim 25, wherein the rotation of the first plurality of top teeth and the second plurality of top teeth cause the first anchor to be fully deployed before the second anchor is fully deployed.

27. An implantable injection port comprising:
   a base having a first anchor opening and a second anchor opening;
   a first gear coupled to the base and rotatable about a first axis, the first gear having a first plurality of gear teeth; and
   a second gear coupled to the base and rotatable about a second axis, the second gear having a second plurality of gear teeth;
   a first anchor coupled to the first gear;
   a second anchor coupled to the second gear;
   a top portion spaced apart from the base having a first plurality of top teeth and a second plurality of top teeth, wherein the first plurality of top teeth are configured to engage with the first plurality of gear teeth on the first gear prior to the second plurality of top teeth engaging with the second plurality of gear teeth on the second gear, the top portion being configured to rotate and cause rotation of the first gear such that the rotation of the first gear causes movement of the first anchor through the first anchor opening of the base prior to movement of the second anchor through the second anchor opening and rotation of the second gear causes movement of the second anchor through the second anchor opening.

28. The injection port of claim 27, wherein movement of the second anchor is subsequent to a beginning of movement of the first anchor.

29. An implantable injection port for use with a gastric band for treating obesity and for attaching to a tissue of a patient, the implantable injection port comprising:
   a base having a first anchor opening and a second anchor opening;
   a top rotatably coupled to the base and spaced from the base, the top rotatable with respect to the base about a longitudinal axis through the top and the base;
   a first anchor coupled to the base and rotatably deployable about a first axis different from the longitudinal axis through the first anchor opening; and
   a second anchor coupled to the base and rotatably deployable about a second axis different from the longitudinal axis through the second anchor opening,
   wherein the first anchor and the second anchor are constructed to be non-simultaneously deployed through their respective anchor openings, and wherein the first and second anchors are constructed to be deployed in response to relative rotation between the top and the base.

30. An implantable injection port for use with a gastric band for treating obesity and for attaching to a tissue of a patient, the implantable injection port comprising:
   a base having a first anchor opening and a second anchor opening;
   a top rotatably coupled to the base and spaced from the base, the top rotatable with respect to the base about a longitudinal axis through the top and the base;
   a first anchor coupled to the base and rotatably deployable about a first axis different from the longitudinal axis through the first anchor opening; and
   a second anchor coupled to the base and rotatably deployable about a second axis different from the longitudinal axis through the second anchor opening,
   wherein the first anchor and the second anchor are constructed to be asynchronously deployed through their respective anchor openings, and wherein the first and second anchors are constructed to be deployed in response to relative rotation between the top and the base.

* * * * *